US011358985B2

(12) United States Patent
Zheng et al.

(10) Patent No.: US 11,358,985 B2
(45) Date of Patent: Jun. 14, 2022

(54) TRIPEPTIDE COMPOUND, PREPARATION METHOD THEREFOR, AND APPLICATION THEREOF

(71) Applicant: NORTHWEST UNIVERSITY, Shaanxi (CN)

(72) Inventors: Xiaohui Zheng, Shaanxi (CN); Yajun Bai, Shaanxi (CN); Fanggang Qin, Shaanxi (CN); Pei Liu, Shaanxi (CN); Jiacheng Fang, Shaanxi (CN); Xirui He, Shaanxi (CN); Xiaoxiao Wang, Shaanxi (CN)

(73) Assignee: NORTHWEST UNIVERSITY, Shaanxi (CN)

( * ) Notice: Subject to any disclaimer, the term of this patent is extended or adjusted under 35 U.S.C. 154(b) by 328 days.

(21) Appl. No.: 15/529,633

(22) PCT Filed: Nov. 27, 2015

(86) PCT No.: PCT/CN2015/095758
§ 371 (c)(1),
(2) Date: May 25, 2017

(87) PCT Pub. No.: WO2016/082786
PCT Pub. Date: Jun. 2, 2016

(65) Prior Publication Data
US 2017/0267718 A1 Sep. 21, 2017

(30) Foreign Application Priority Data
Nov. 27, 2014 (CN) .......................... 201410705180.3

(51) Int. Cl.
*A61K 38/00* (2006.01)
*A61K 38/06* (2006.01)
*C07K 5/083* (2006.01)
*C07K 5/068* (2006.01)
*C07K 5/078* (2006.01)
*C07K 5/062* (2006.01)
*C07K 5/06* (2006.01)
*C07K 5/072* (2006.01)
*C07K 5/065* (2006.01)

(52) U.S. Cl.
CPC ............ *C07K 5/0806* (2013.01); *A61K 38/06* (2013.01); *C07K 5/0606* (2013.01); *C07K 5/06017* (2013.01); *C07K 5/06026* (2013.01); *C07K 5/06034* (2013.01); *C07K 5/06043* (2013.01); *C07K 5/06078* (2013.01); *C07K 5/06086* (2013.01); *C07K 5/06095* (2013.01); *C07K 5/06104* (2013.01); *C07K 5/06139* (2013.01); *C07K 5/06156* (2013.01); *C07K 5/06191* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 4,314,936 A | 2/1982 | Yaron et al. | |
| 4,525,301 A | 6/1985 | Henning et al. | |
| 5,011,825 A | 4/1991 | Konig et al. | |
| 5,990,177 A * | 11/1999 | Brown | A61P 25/28 514/729 |
| 2005/0288232 A1 | 12/2005 | Furuishi et al. | |
| 2006/0063941 A1 | 3/2006 | Rao et al. | |
| 2009/0131677 A1 | 5/2009 | Zheng et al. | |

FOREIGN PATENT DOCUMENTS

| | | |
|---|---|---|
| CN | 1939912 | * 10/2005 |
| CN | 1868998 A | 11/2006 |
| CN | 1939912 | 4/2007 |
| CN | 101607907 A | 12/2009 |
| CN | 102757479 A | 10/2012 |
| CN | 104945469 A | 9/2015 |
| DE | 3315464 A1 | 10/1984 |
| DE | 252191 A1 | 12/1987 |
| DE | 3839127 A1 | 5/1990 |
| EP | 0249169 A2 | 12/1987 |
| EP | 1661909 A1 | 5/2006 |
| JP | 2013159577 A | 8/2013 |
| JP | 2014141462 A | 8/2014 |
| RU | 2339645 C2 | 11/2008 |
| WO | 2004024754 A1 | 3/2004 |
| WO | 2010124201 A2 | 10/2010 |

OTHER PUBLICATIONS

Grover et al. (J Pharmacol Exp Ther. Jun. 1991;257(3):919-29) (Year: 1991).*
Johnston et al. (J Cardiovasc Pharmacol. 1986;8 Suppl 1 :S9-14, abstract only) (Year: 1986).*
See "Tufts Medical center" (downloaded from URL:< https://hhma.org/healthadvisor/aha-secondht-car/>) (Year: 2021).*
B.U. Bridge (Keeping the pressure off, Oct. 17, 1997, vol. 1, No. 8) (Year: 1997).*
New Zealand First Examination Report corresponding to Patent No. 732301; dated Nov. 6, 2017.
G. Wang et al., "Preparation of L-proline based aeruginosin 298-A analogs: Optimization of the P1-moiety," Bioorganic & Medical Chemistry Letters, 2009, pp. 3798-3803.

(Continued)

*Primary Examiner* — Sergio Coffa

(74) *Attorney, Agent, or Firm* — Cantor Colburn LLP

(57) ABSTRACT

Provided are a tripeptide compound, a preparation method therefor, and an application thereof. The structure of the related compound is represented by formula (I). The provided compound has angiotensin converting enzyme inhibiting bioactivity, and the compound and a pharmaceutical composition thereof play a role in preventing and treating hypertension and other cardiocerebral vascular system diseases.

6 Claims, 2 Drawing Sheets

(56) References Cited

OTHER PUBLICATIONS

H. Liu et al., "Total Synthesis and Biological Evaluation of Grassypeptolide A," Chemistry: A European Journal, 2013, pp. 6774-6784, vol. 19.
International Search Report corresponding to Application No. PCT/CN2015/095758; dated Feb. 29, 2016.
Boon, P.J. et al: "Semisynth. Pept. Proteins, Pap. Int. Meet. Protein Semisynth. (1978), Meeting Date 1977, 115-26. Editor(s): Offord, R. E.; DiBello, C.", XP002781667.
Extended European Search Report corresponding to Application No. 15863217.4-1109/3225627 PCT/CN2015095758; dated Jul. 20, 2018.
Francesco Chillemi, "Synthesis of Human Growth Hormone-27-44)—octadecapeptide and some Smaller Fragment Peptides," Department of Organic Chemistry, University of Milan; Milan, Italy 1913-1917.
G. Radau et al., "New Cyanopeptide-Derived Low Molecular Weight Thrombin Inhibitors," Arch. Pharm. Pharm. Med. Chem.; 2003, vol. 336, No. 8, Aug. 1, 2003, pp. 372-380.
P.B.W. Ten Kortenaar et al., "Semisynthesis of horse heart cytochrome c analogues from two or three fragments". Proc. Natl. Acad. Sci. USA; vol. 82, pp. 8279-8283, Dec. 1985.
P.J. Boon et al., "Semisynthesis of the native sequence of horse heart cytochrome c-(66-104)-nonatriacontapeptide," Int. J. Peptide Protein Res.; 28, 1986, pp. 477-492.
P.J. Boon et al., Database Capblus [online]; Chemical Abstracts Service, Columbus OH, US. 1984, XP002783025.
Australian IP Office Action corresponding to Application No. 2015353118; dated Mar. 1, 2018.
Canadian Office Action corresponding to Application No. 2968595; dated Mar. 27, 2018.
Wharton et al., "The Synthesis of Peptide β-Lactams as Potential Protease Inhibitors," Journal of the Chemical Society; 1984, pp. 27-39.
Flynn et al., "The Synthesis of an Aminophosphonic Acid Converting Enzyme Inhibitor," Merrel Dow Research Institute; pp. 1757-1758.
Fournie-Zaluski et al., "Design of Orally Active Dual Inhibitors of Neutral Endopeptidase and Angiotension-Converting Enzyme with Long Duration of Action," J.Med. Chem., 1996, pp. 2594-2608.
Galardy, "Inhibition of Angiotensin Converting Enzyme of Phosphonic Amides and Phosphonic Acids," Biochemistry; vol. 22, No. 8, 1983; pp. 1990-1995.
Summary of the JP Office Action corresponding to Application No. 2017-527865; dated Jun. 19, 2018.
Intellectual Property Office of Singapore Written Opinion corresponding to Application No. 11201704235S; dated Jul. 6, 2018.
Russian First Office Action corresponding to Application No. 2017121590; dated May 17, 2018.
Radau et al., "Design and X-ray crystal structures of human thrombin with synthetic cyanopeptide-analogues"; Pharmazie, 2007, 62(2), 83-88 DOI: 10.1691/ph.2007.2.6619.
KIPO Notification of Reason for Refusal corresponding to Application No. 10-2017-7017351; dated Jun. 28, 2019.
SIPO First Office Action corresponding to Application No. 201410705180.3; dated Sep. 18, 2018.

* cited by examiner

TRIPEPTIDE COMPOUND, PREPARATION METHOD THEREFOR, AND APPLICATION THEREOF

This present application is the U.S. national stage of application No. PCT/CN2015/095758, titled 'TRIPEPTIDE COMPOUND, PREPARATION METHOD THEREFOR, AND APPLICATION THEREOF", filed on Nov. 27, 2015, which claims priority under 35 U.S.C. § 119(a) and 35 U.S.C. § 365(b) from Chinese Application No. 201410705180.3, titled 'TRIPEPITIDE COMPOUND, PREPARATION :METHOD THEREFOR, AND APPLICATION THEREOF", filed on Nov. 27, 2014, with the State Intellectual Property Office of the People's Republic of China, both of which are incorporated herein by reference in entirety.

FIELD

The present invention relates to novel compounds of formula (I) and corresponding pharmaceutically acceptable salts. The present invention also relates to a method for preparing the compounds or corresponding salts or intermediates thereof. The present invention also relates to a pharmaceutical composition of the compounds. The compounds have angiotensin converting enzyme inhibiting bioactivity, and the compounds and a pharmaceutical composition thereof play a role in preventing and treating hypertension and other cardiocerebral vascular system diseases.

BACKGROUND

The theme of World Health Day 2013 is to control hypertension. According to the survey data published by the World Health Organization (WHO), hypertension and its associated complications have become one of the major diseases that threaten human life and health, with a morbidity and mortality that have exceeded tumor diseases and rank first. There are about 1 billion hypertensive patients worldwide, resulting in 7.1 million cases of cardiovascular death each year, and if not controlled, in 2025 the number of patients will increase to 1.56 billion. Chronic Noncommunicable Disease Prevention and Control Center of the Chinese Center For Disease Control And Prevention has published the latest research results—in 2010, the prevalence of hypertension in Chinese adults was as high as 33.5%, and the total number of people with the disease was estimated to have exceeded 330 million. Hypertension is the most important risk factor for the morbidity and mortality of heart disease, stroke, kidney disease and diabetes. About 2 million deaths per year are associated with hypertension, and hypertension has become an important public health problem. (China News Network, Oct. 10, 2010 16:26) Hypertension and its complications have brought great economic burden to the society and families. So far, great progress has been made in the study of treatment of hypertension and its complications, but the pain of hypertensive patients can still not be completely solved. At the same time, the widespread hazards of hypertension and its complications have led to rapid development of the antihypertensive drug market. Over the past 30 years, hypertension is mostly treated by medicaments, and six categories of antihypertensive drugs, including diuretics, β-receptor blockers, α-receptor blockers, calcium antagonists (CCB), angiotensin converting enzyme inhibitors (ACEI), and angiotensin receptor antagonist (ARB), as well as their different combinations have gradually developed.

For angiotensin converting enzyme inhibition (ACEI), since the advent of captopril in 1981, design of drug using proline as the parent nucleus and targeting angiotensin converting enzyme (ACE, a zinc ion-containing exopeptidase) has being a research hotspot in the field of antihypertensive, and ACEI drugs and lead compounds of dipeptides and tripeptides containing thiol, carboxylic acid, phosphoric acid and other key functional groups have been designed successfully. So far, at least 17 ACEI drugs have become clinical first-line drugs for hypertension treatment. Other antihypertensive drugs have different emphasis, especially ARB antihypertensive drugs have gradually become an important part of antihypertensive drugs due to their long-acting effects and low side effects. However, in clinical cases, hypertensive patients are often accompanied by diabetes, kidney disease and other cardiovascular and cerebrovascular diseases. Only one antihypertensive drug often cannot achieve a desirable effect, so the combination of two or more antihypertensive drugs has become a trend of clinical antihypertensive drugs. Therefore, it is a trend to develop a multi-effect antihypertensive drugs which are more effective and suitable for multiple indications.

SUMMARY

The present invention provides a tripeptide compound with a structure of formula (I)

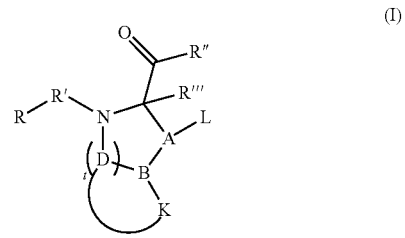

(I)

wherein, in formula (I),
R is represented by formula (II)

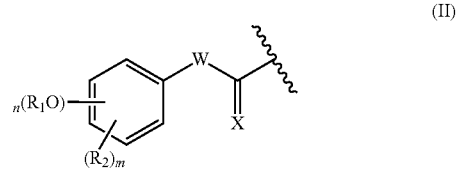

(II)

wherein, in formula (II).
$R_1$ is selected from hydrogen, alkyl, cycloalkyl, heteroalkyl, heterocyclyl, alkenyl, alkynyl, acyl, aroyl, aryl, aralkyl, heteroaryl or heteroaralkyl:

$R_2$ is selected from hydrogen, alkyl, cycloalkyl, heteroalkyl, heterocyclyl, alkenyl, alkynyl, acyl, aroyl, aryl, aralkyl, heteroaryl, heteroaralkyl, alkylthio, aralkylthio, arylthio, F, Cl, Br, I, $NO_2$ or CN:

$R_1$ and $R_2$ are the same or different;

n=0, 1, 2, 3, 4, or 5; and when n≥2, multiple $R_1$s are the same or different;

m=0, 1, 2, 3, 4, or 5; and when m≥2, multiple $R_2$s are the same or different;

W is selected from

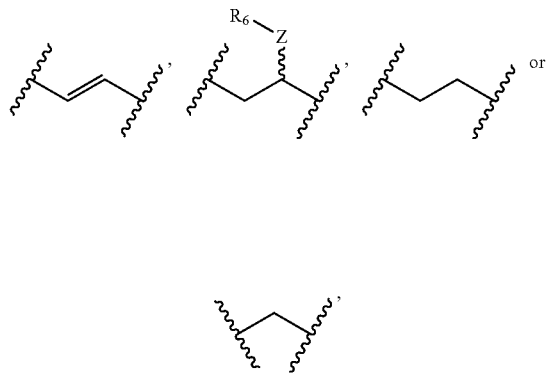

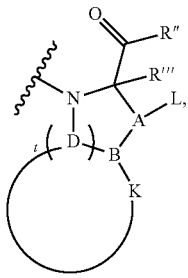

is linked to the N-terminus of and the N-terminus of wherein

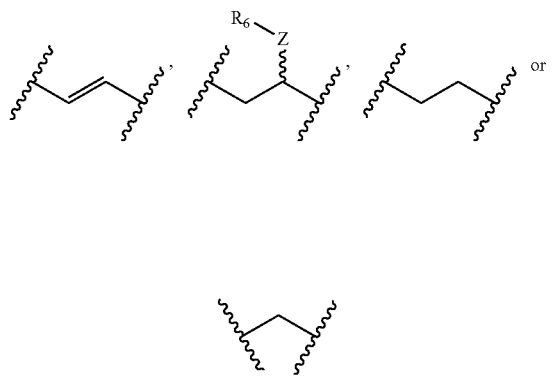

is linked to the C-terminus of

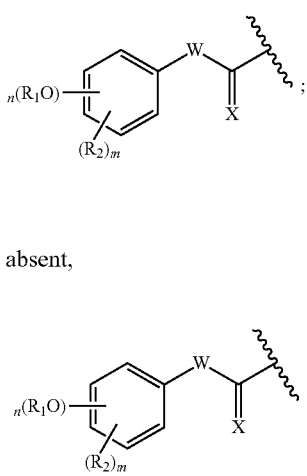

and
when R' is absent, is linked to the benzene ring on the left side thereof; wherein Z is selected from oxygen or nitrogen, and $R_6$ is selected from hydrogen, alkyl, cycloalkyl, heteroalkyl, heterocyclyl, alkenyl, alkynyl, aryl, aralkyl, heteroaryl or heteroaralkyl; and X is selected from oxygen or hydrogen;
wherein, in formula (I),
R' is a residue of an L- or D-amino acid or amino acid derivative, as shown in formula (III), or R' is absent, and

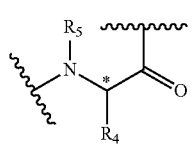 (III)

is linked to when R' is a residue of an L- or D-amino acid or amino acid derivative, the C-terminus of

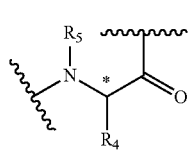

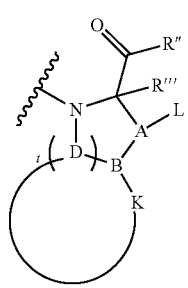

via an amide bond or a C—N bond; and
wherein $R_4$ and $R_5$ are each independently selected from hydrogen, alkyl, cycloalkyl, heteroalkyl, heterocyclyl, alkenyl, alkynyl, aryl, aralkyl, heteroaryl or heteroaralkyl; and $R_4$ and $R_5$ are the same or different;

wherein, in formula (I),
R'' is represented by the formula (IV):

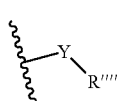
(IV)

wherein:
Y is selected from oxygen, nitrogen or sulfur, and
when Y is nitrogen, R'''' is $R^7$ and $R^8$, and R'' is

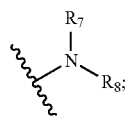

when Y is oxygen, R'''' is $R^9$, and R'' is —$OR^9$;
when Y is sulfur, R'''' is $R^{10}$, and R'' is —$SR^{10}$:
wherein, $R^7$, $R^8$, $R^9$ and $R^{10}$ may be the same or different, and are each independently selected from hydrogen, alkyl, cycloalkyl, heteroalkyl, heterocyclyl, alkenyl, alkynyl, aryl, aralkyl, heteroaryl or heteroaralkyl;
wherein, in formula (I),
R''' is selected from hydrogen or alkyl;
A=carbon:
L is selected from hydrogen, alkyl, substituted alkyl, aryl or substituted aryl;
D is carbon or absent, t=0, 1, 2, 3; and
when D is carbon and B is carbon, A is linked to B by a carbon-carbon double bond or carbon-carbon single bond, and K and B and D are in a ring system; or A is linked to B by a carbon-carbon double bond or carbon-carbon single bond, and K is linked to B and is not linked to D;
wherein K and B and D are in a ring system, K is a selected from an alkyl or a heteroalkyl with a carbon atom number of 2 to 8, or an alkenyl with a carbon atom number of 3 to 8, or K together with B and D is formed into an aryl, a substituted aryl, a heteroaryl or a substituted heteroaryl;
when K is linked to B and is not linked to D, K is selected from hydrogen, alkyl, heteroalkyl, cycloalkyl, heterocyclyl, alkenyl, alkynyl, hydroxy, alkoxy, aryloxy aryl, aralkyl, heteroaryl or heteroaralkyl;
when D is carbon and B is sulfur, A is linked to B via a carbon-sulfur single bond, and K is absent; and
when D is absent, B is carbon, and K is hydrogen;
wherein the alkyl, cycloalkyl, heteroalkyl, heterocyclyl, alkenyl, alkynyl, aryl, aralkyl, heteroaryl and heteroaralkyl groups may each be unsubstituted or optionally substituted with one or more substituents selected from hydroxy, alkoxy, aryloxy, thio, thioalkyl, arylthio, amino, amido, alkylamino, arylamino, alkylsulfonyl, arylsulfonyl, sulfonamido, alkyl, aryl, heteroaryl, alkylsulfonamido, arylsulfonamido, keto, carboxy, alkoxycarbonyl, carboxamido, alkoxycarbonylamino, alkoxycarbonyloxy, alkylureido, arylureido, halo, cyano or nitro group.

Optionally, R group

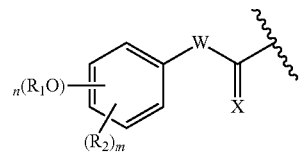
(II)

is selected from the following structures:

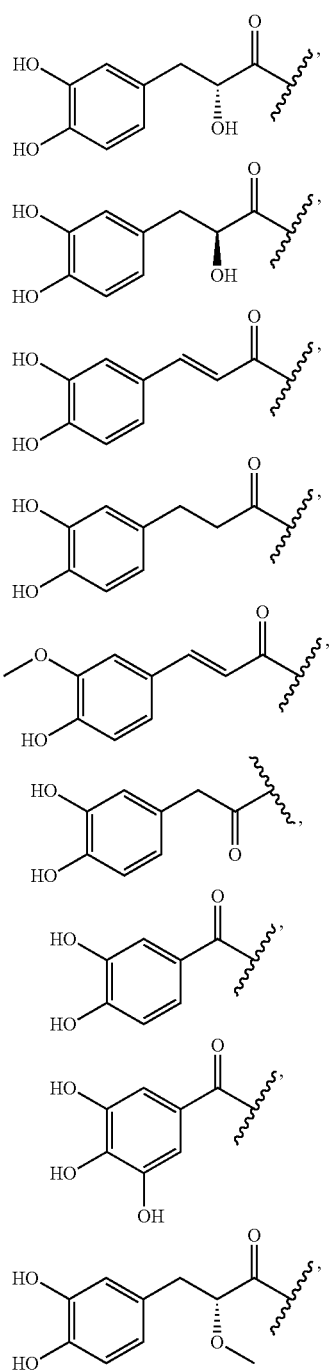

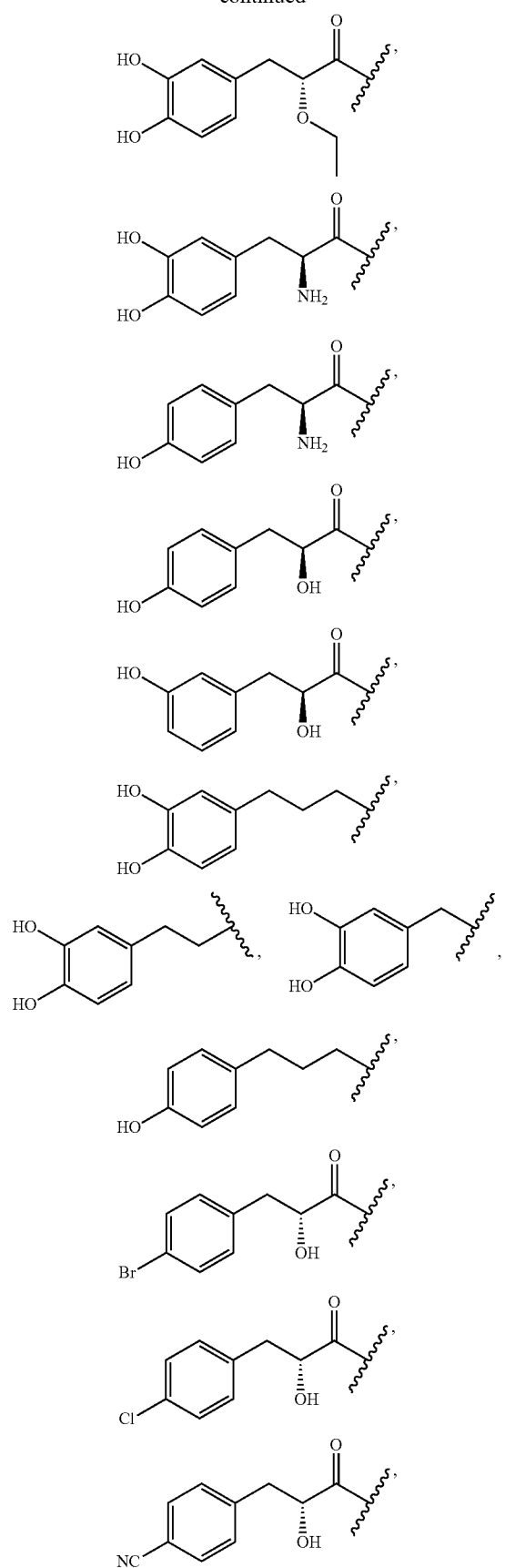
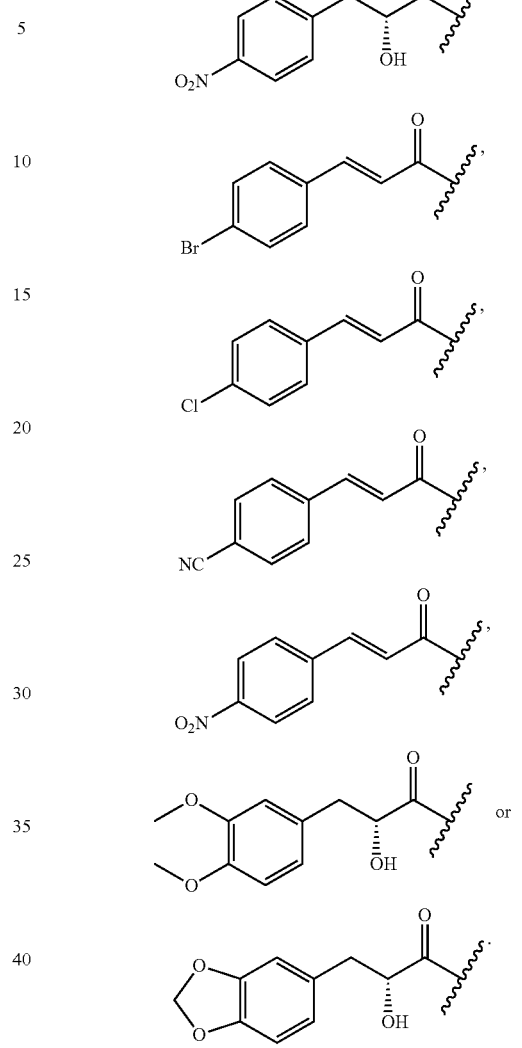
Optionally, R' group
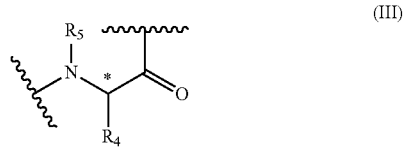
is selected from the following structures:
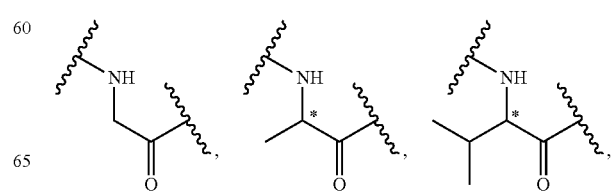

-continued
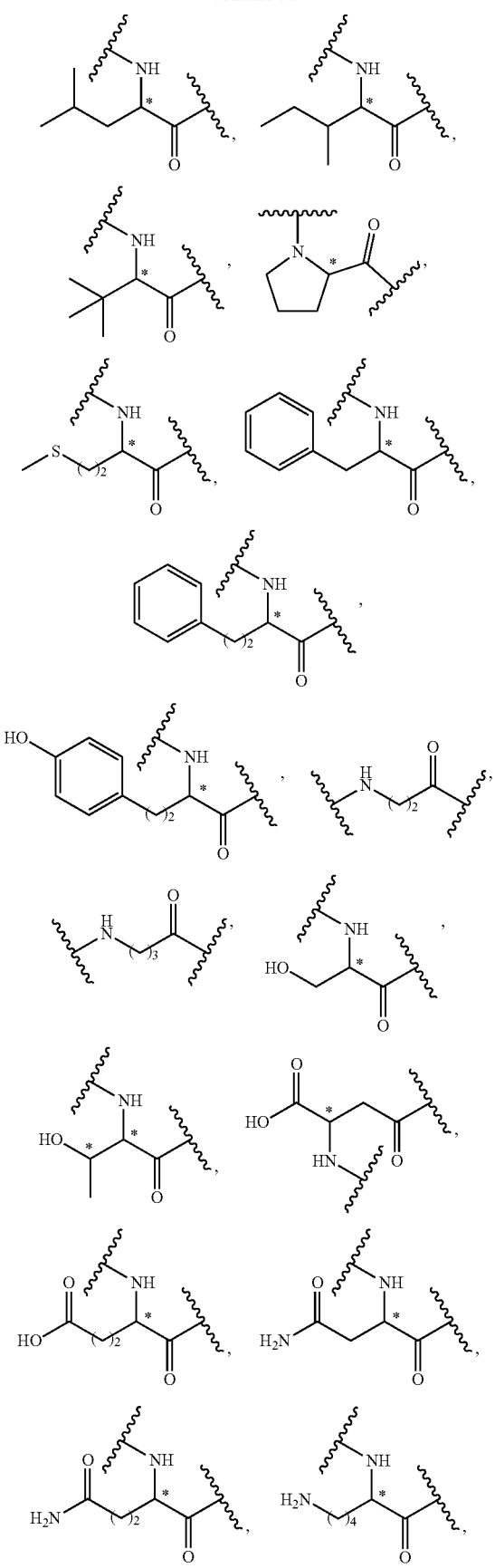
-continued
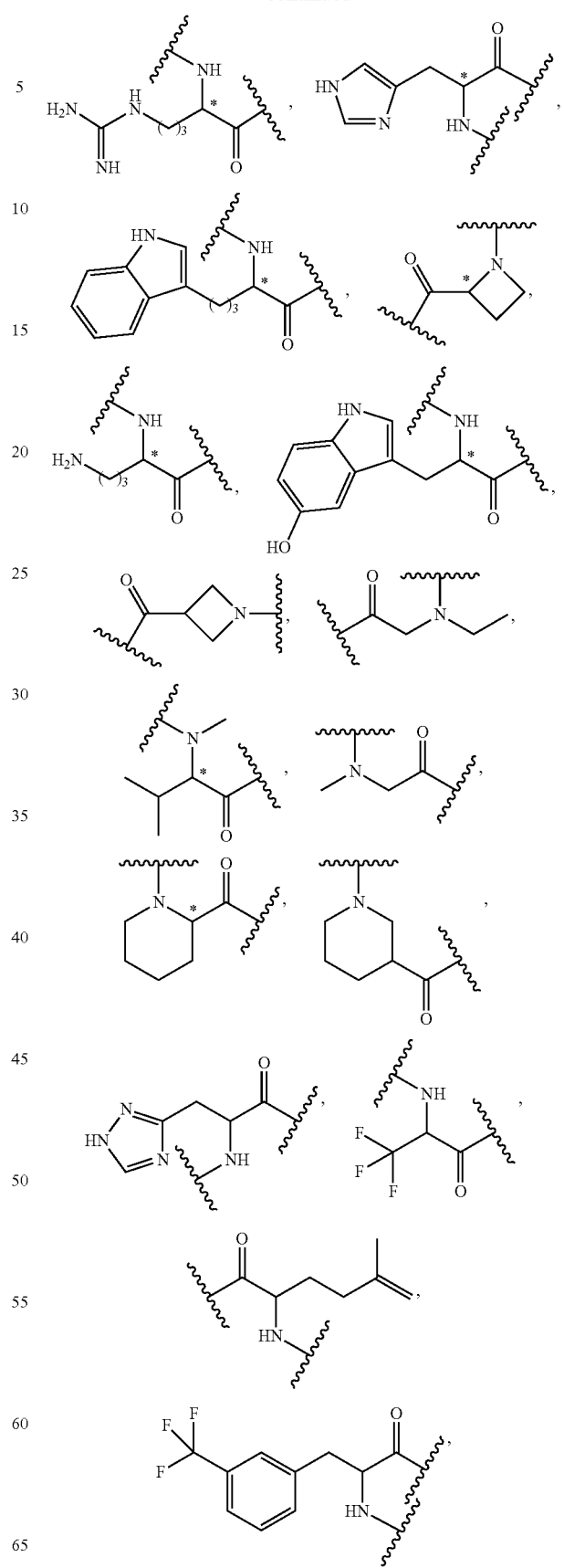

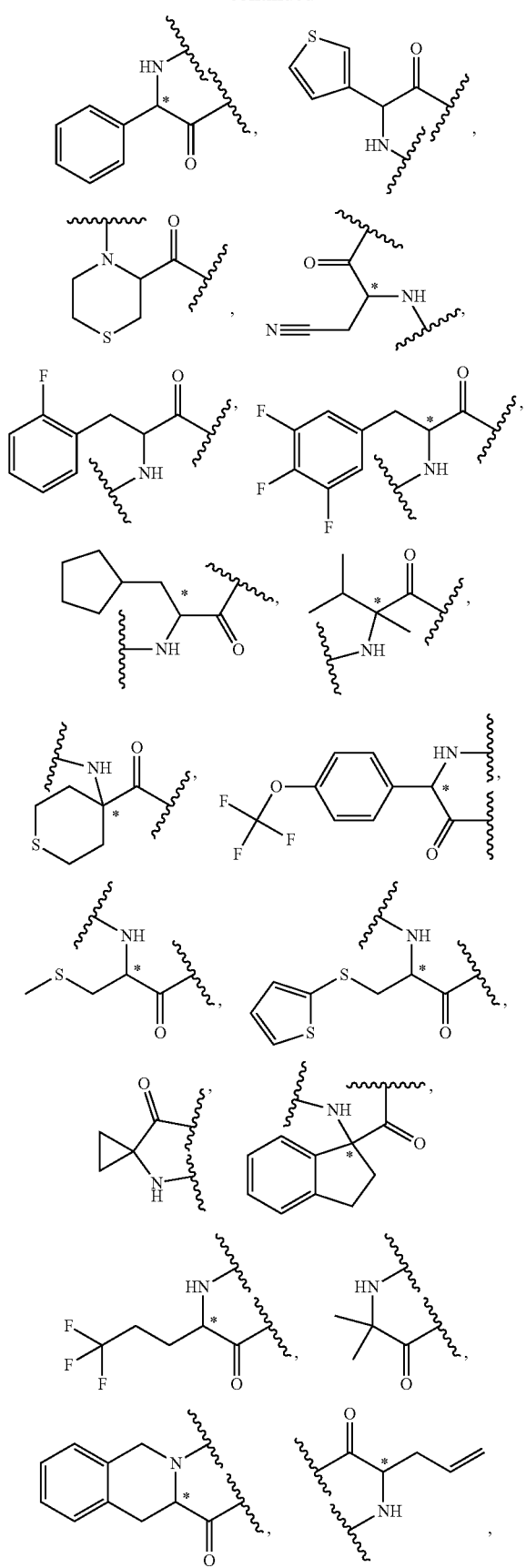
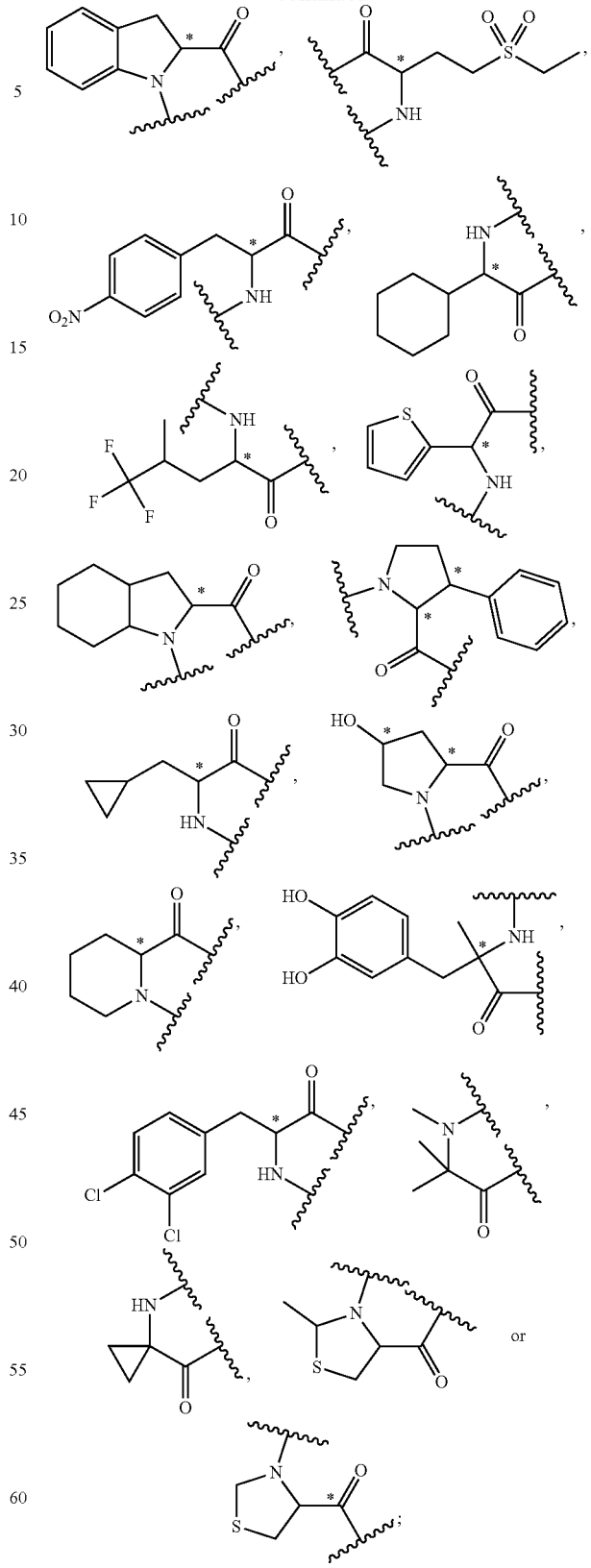
wherein, "*" represents a chiral center, and the compound comprising "*" includes all chiral isomers of the structural formula.

Optionally, when Y is oxygen, $R^9$ is a group selected from:
methyl, ethyl, propyl, isopropyl, n-butyl, isobutyl, tert-butyl, n-pentyl, cyclopropyl, cyclobutyl, cyclopentyl, cyclohexyl, cycloheptyl or the following structures:
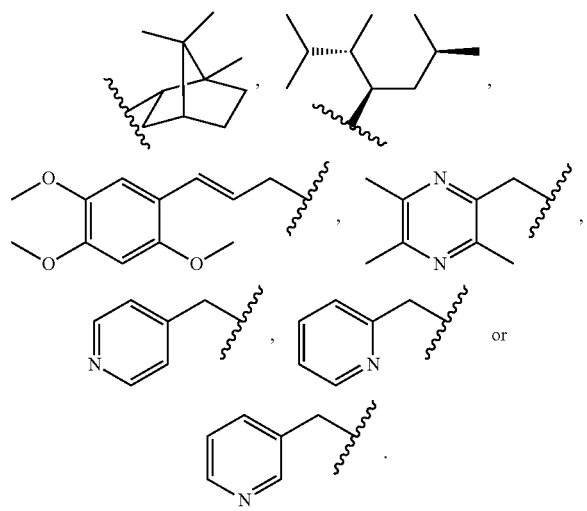
Optionally, when Y is nitrogen, R" is a group selected from
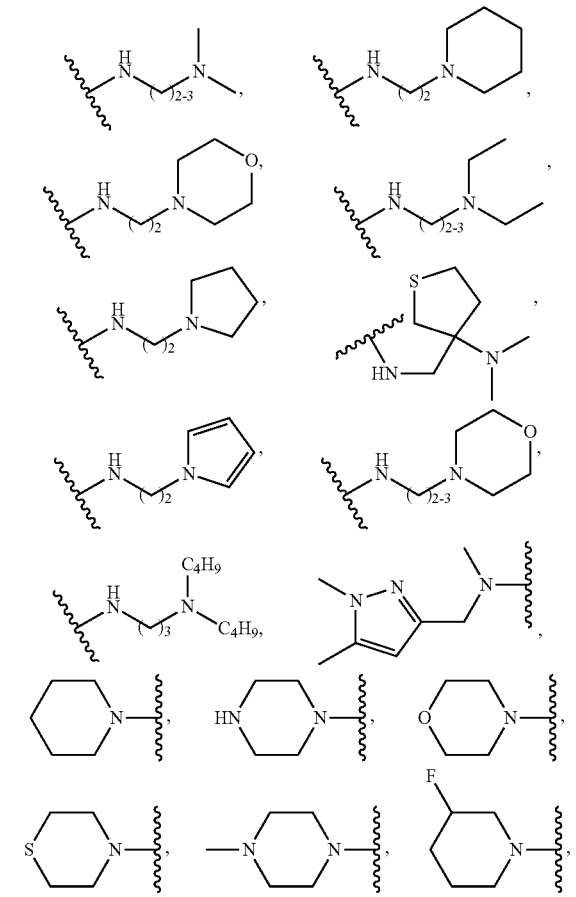
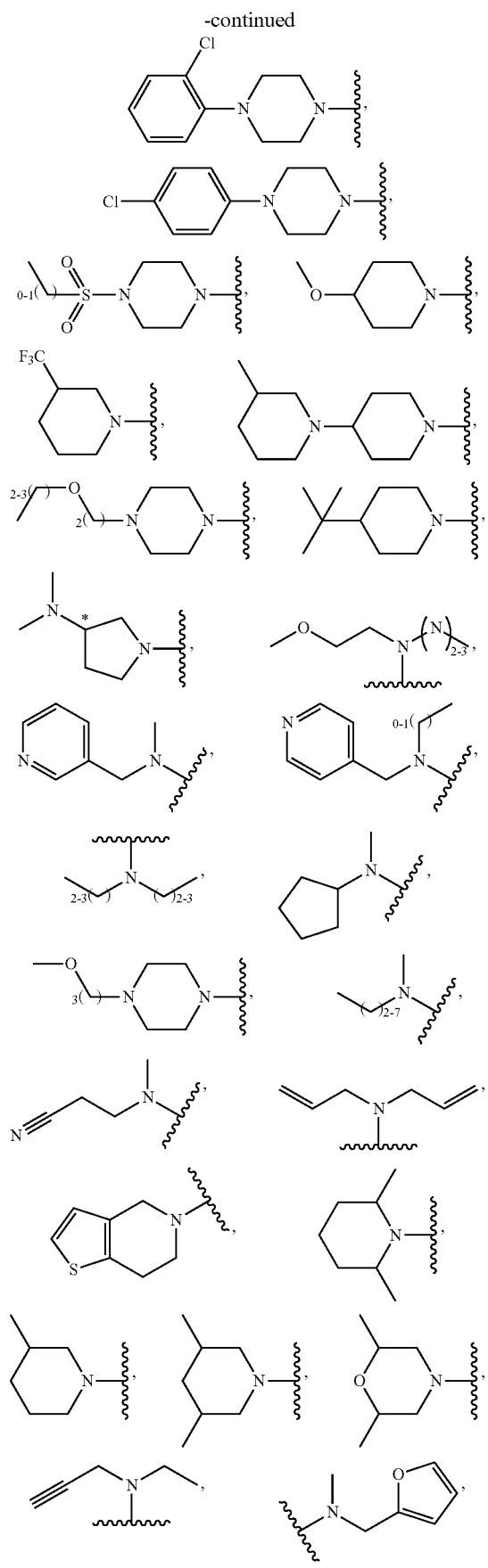

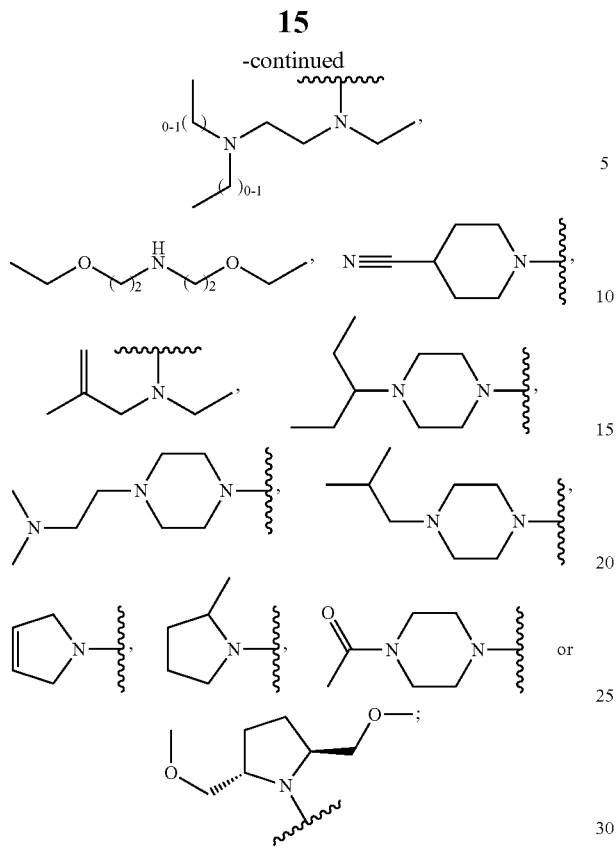

wherein, "*" represents a chiral center, and the compound comprising "*" includes all chiral isomers of the structural formula.

Optionally, when Y is sulfur, R" is a group selected from

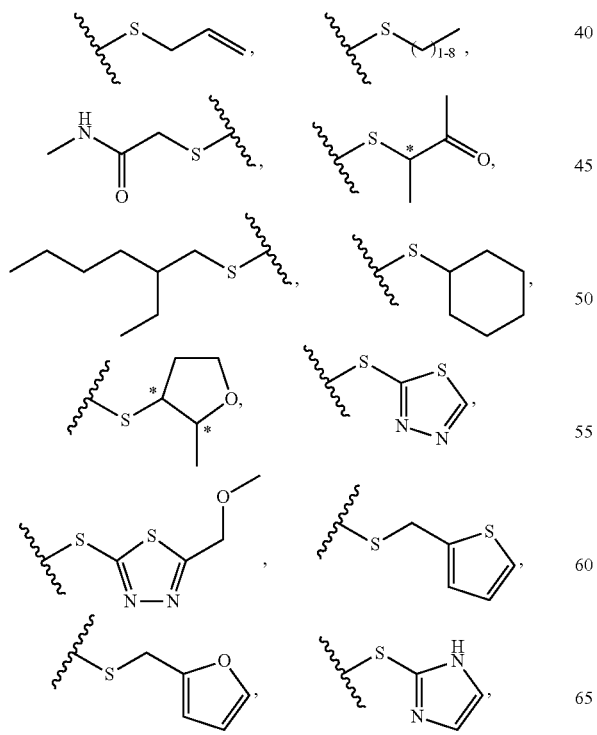

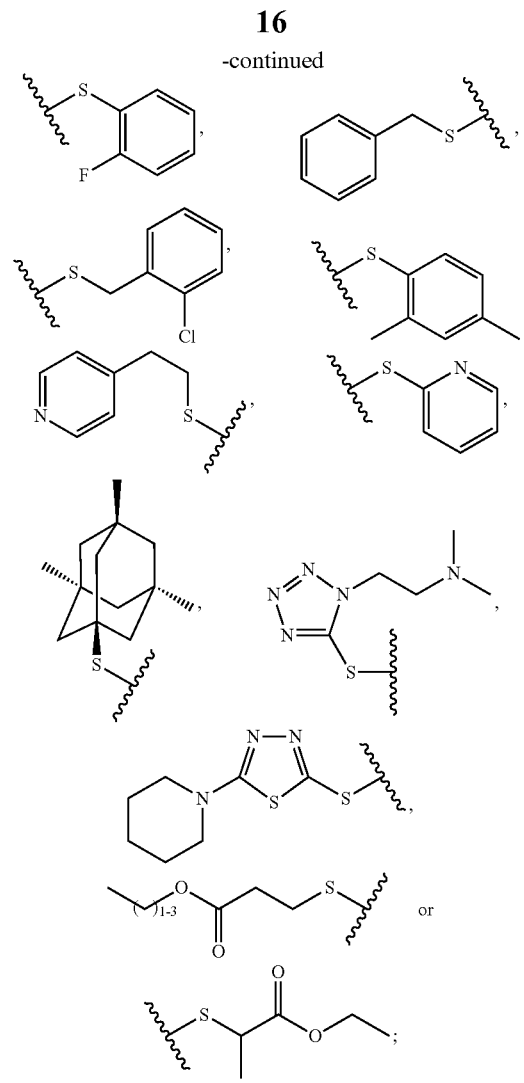

wherein, "*" represents a chiral center, and the compound comprising "*" includes all chiral isomers of the structural formula.

Optionally, formula (I) is selected from the following formula structures:

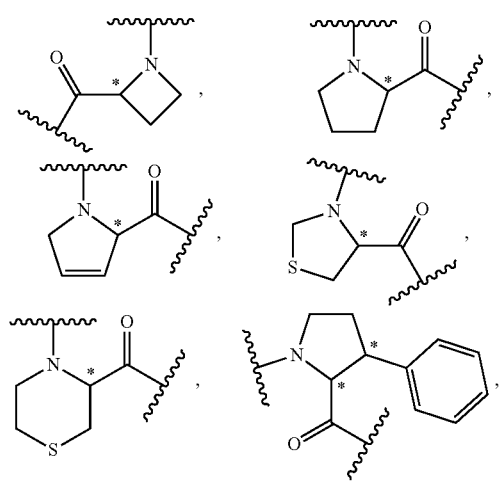

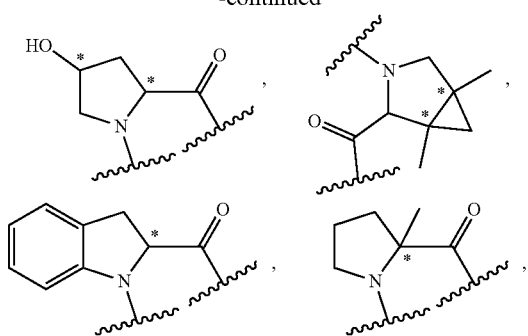
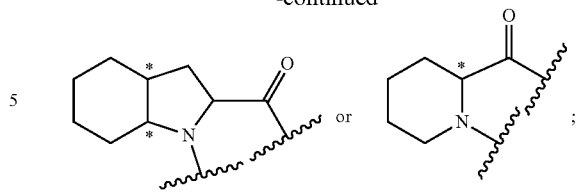
wherein, "*" represents a chiral center, and the compound comprising "*" includes all chiral isomers of the structural formula.
Optionally, the tripeptide compound mentioned above is selected from the compounds of the following structures:
| No. | formula |
|---|---|
| 221S-1 | |
| 221S-2 | |
| 221S-3 | |
| 221S-4 | |
| 221S-5 | |

-continued

| No. | formula |
|---|---|
| 221S-6 | |
| 221S-7 | |
| 221S-8 | |
| 221S-9 | |
| 221S-10 | |
| 221S-11 | |

-continued

| No. | formula |
|---|---|
| 221S-12 | |
| 221S-13 | |
| 221S-14 | |
| 221S-15 | |
| 221S-16 | |
| 221S-17 | |

-continued
| No. | formula |
|---|---|
| 221S-18 | 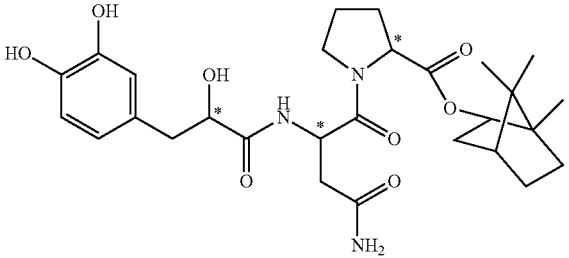 |
| 221S-19 | 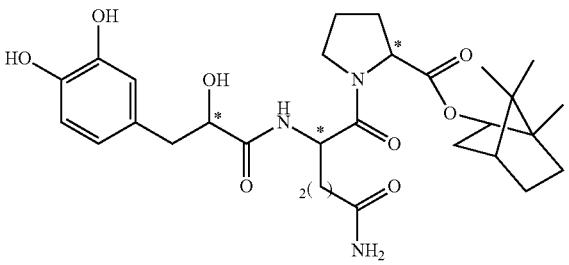 |
| 221S-20 | 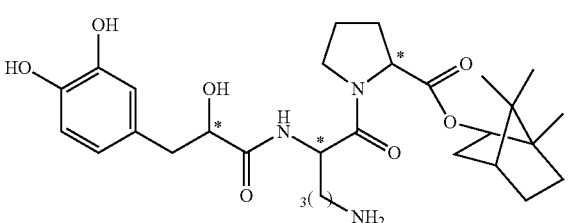 |
| 221S-21 | 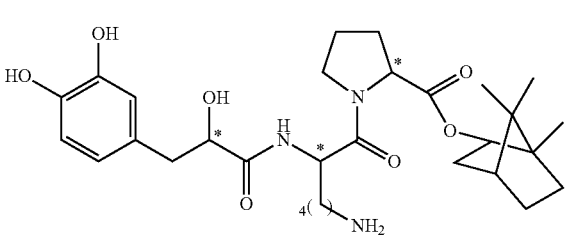 |
| 221S-22 | 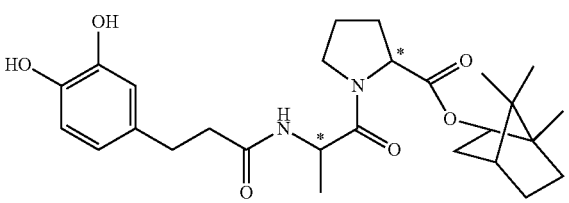 |
| 221S-23 | 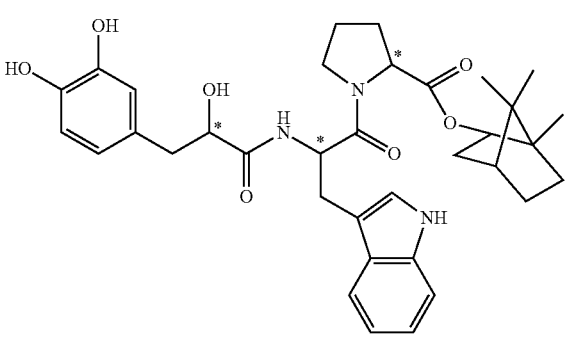 |

-continued

| No. | formula |
|---|---|
| 221S-24 | (chemical structure) |
| 221S-25 | (chemical structure) |
| 221S-26 | (chemical structure) |
| 221S-27 | (chemical structure) |
| 221S-28 | (chemical structure) |
| 221S-29 | (chemical structure) |

-continued

| No. | formula |
|---|---|
| 221S-30 | |
| 221S-31 | |
| 221S-32 | |
| 221S-33 | |
| 221S-34 | |
| 221S-35 | |
| 221S-36 | |

-continued
| No. | formula |
|---|---|
| 221S-37 |  |
| 221S-38 |  |
| 221S-39 |  |
| 221S-40 |  |
| 221S-41 |  |
| 221S-42 |  |

-continued

| No. | formula |
|---|---|
| 221S-43 | |
| 221S-44 | |
| 221S-45 | |
| 221S-46 | |
| 221S-47 | |

-continued
| No. | formula |
|---|---|
| 221S-48 | 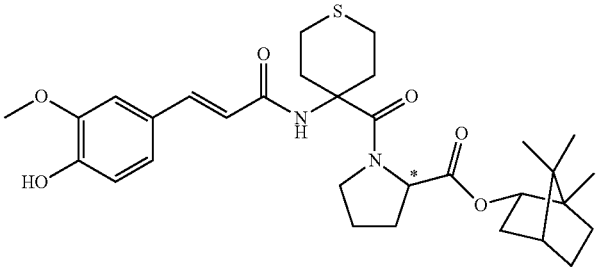 |
| 221S-49 | 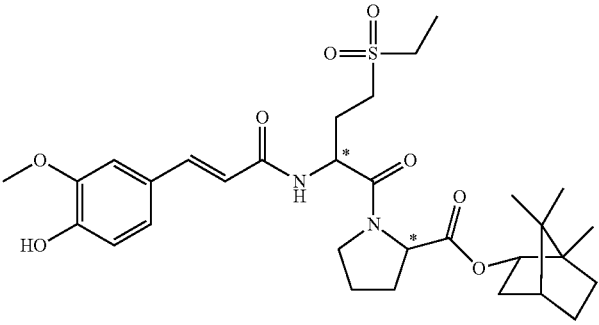 |
| 221S-50 | 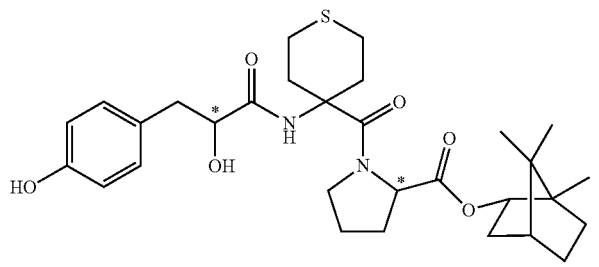 |
| 221S-51 | 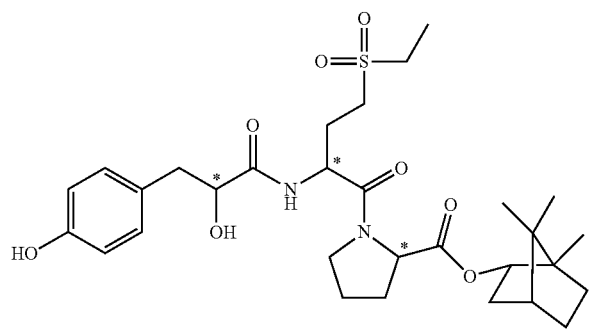 |
| 221S-52 | 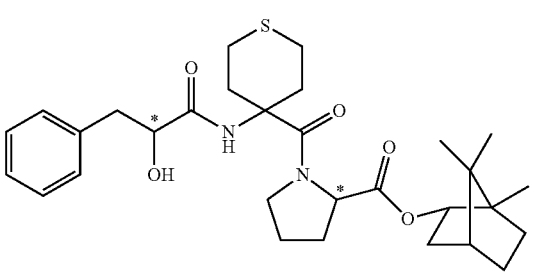 |

-continued
| No. | formula |
|---|---|
| 221S-53 | 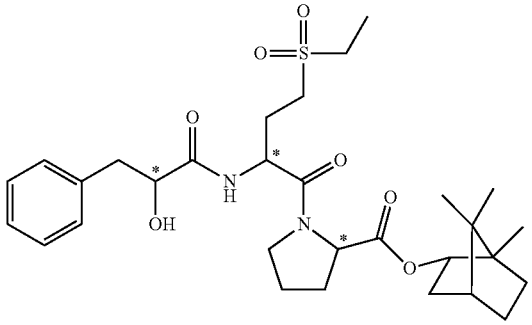 |
| 221S-54 | 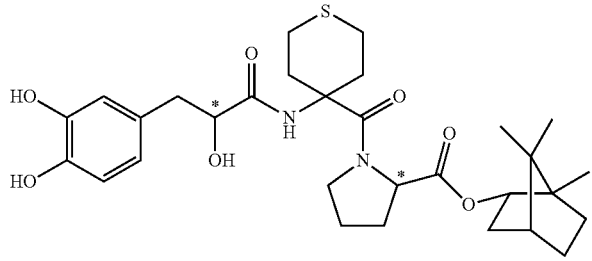 |
| 221S-55 | 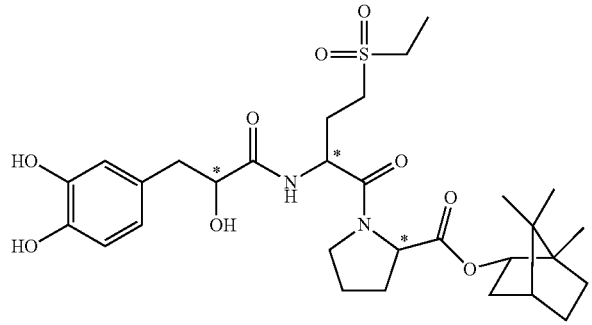 |
| 221S-56 | 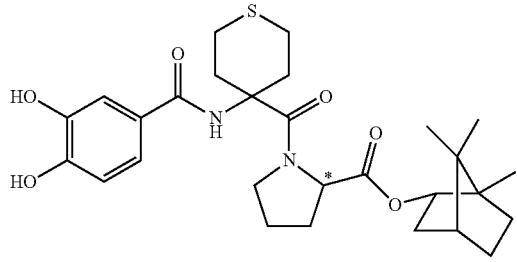 |
| 221S-57 | 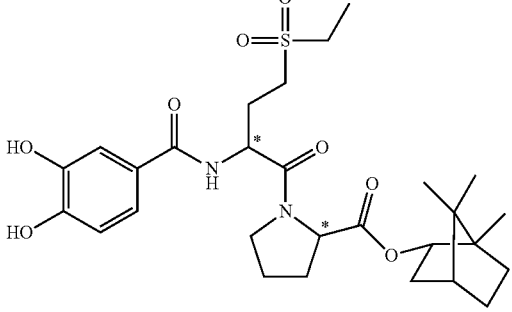 |

-continued
| No. | formula |
|---|---|
| 221S-58 | 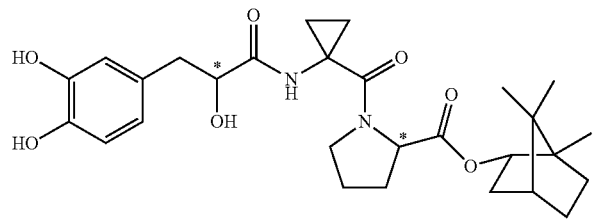 |
| 221S-59 | 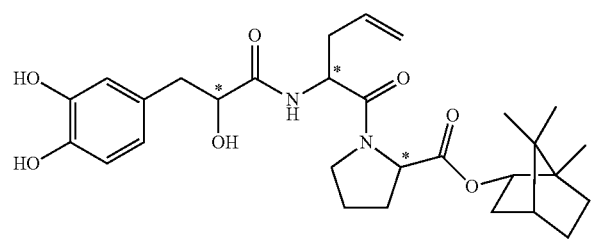 |
| 221S-60 | 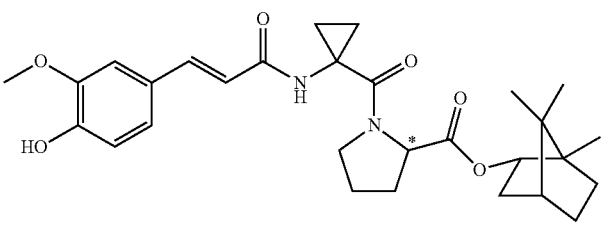 |
| 221S-61 | 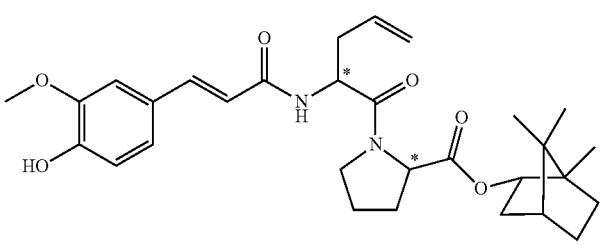 |
| 221S-62 | 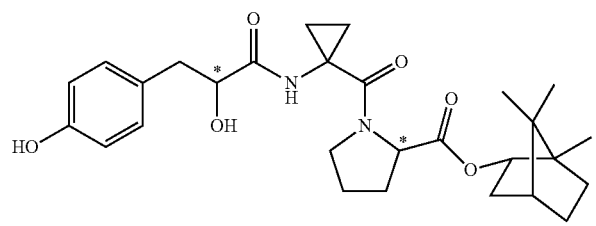 |
| 221S-63 | 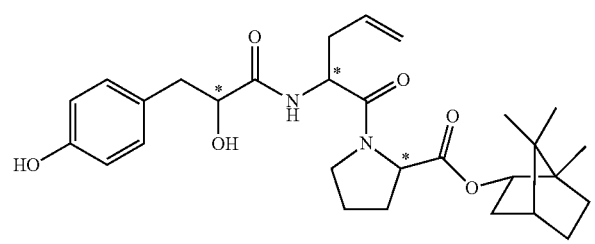 |

| No. | formula |
|-----|---------|
| 221S-64 | |
| 221S-65 | |
| 221S-66 | |
| 221S-67 | |
| 221S-68 | |
| 221S-69 | |

| No. | formula |
|---|---|
| 221S-70 | 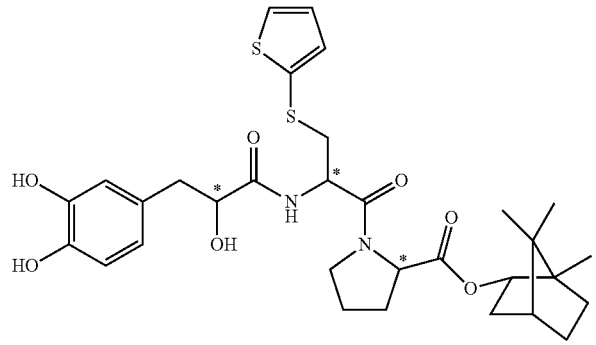 |
| 221S-71 | 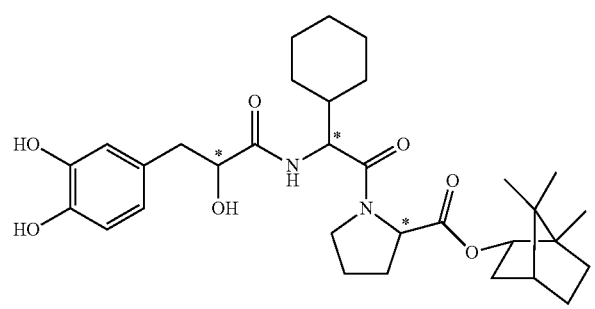 |
| 221S-72 | 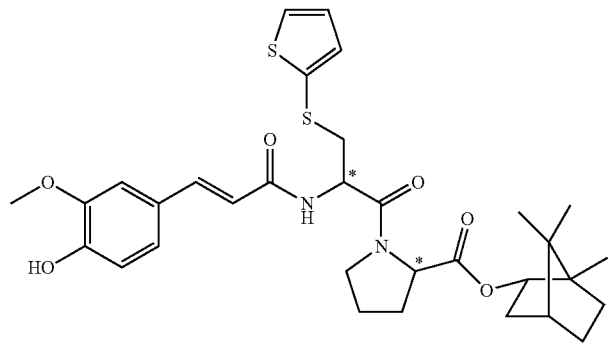 |
| 221S-73 | 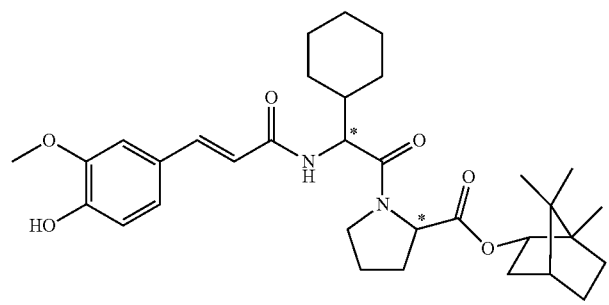 |

| No. | formula |
|---|---|
| 221S-74 | |
| 221S-75 | |
| 221S-76 | |
| 221S-77 | |

-continued

| No. | formula |
|---|---|
| 221S-78 | |
| 221S-79 | |
| 221S-80 | |
| 221S-81 | |
| 221S-82 | |

-continued
| No. | formula |
|---|---|
| 221S-83 | 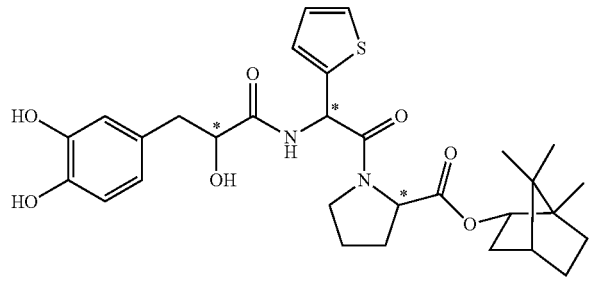 |
| 221S-84 | 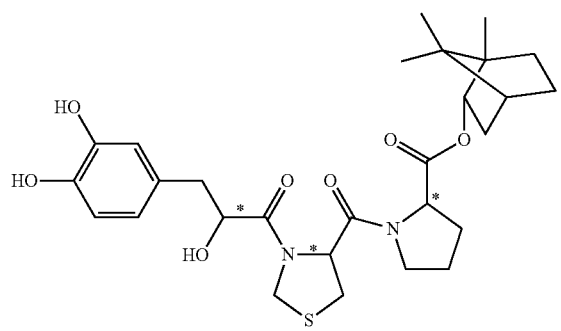 |
| 221S-85 | 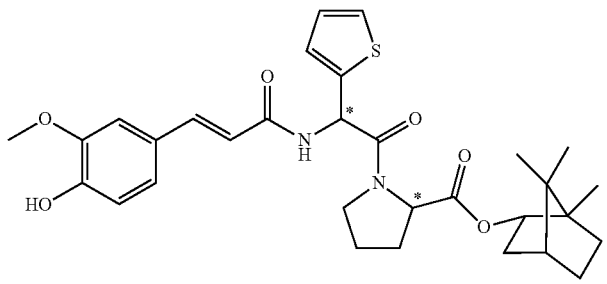 |
| 221S-86 | 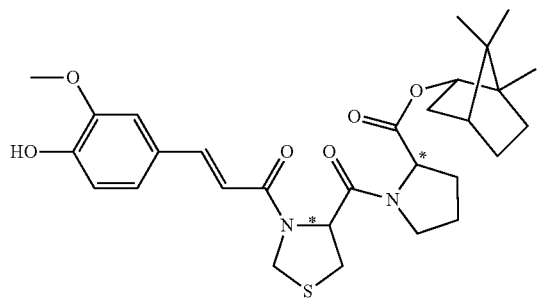 |
| 221S-87 | 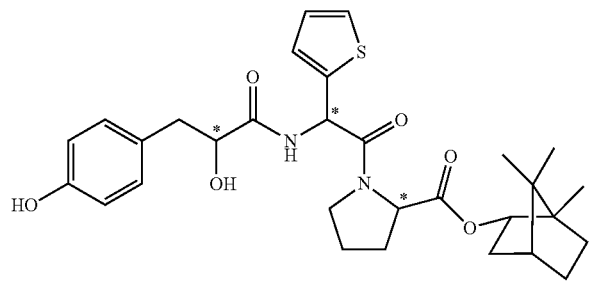 |

| No. | formula |
|---|---|
| 221S-88 | 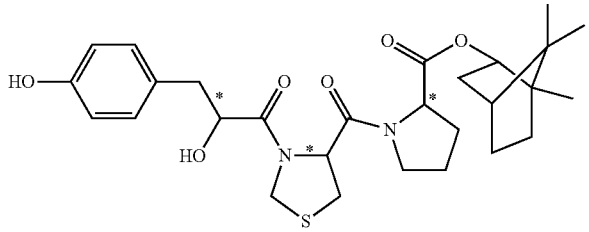 |
| 221S-89 | 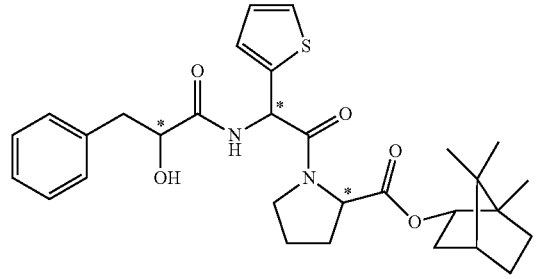 |
| 221S-90 | 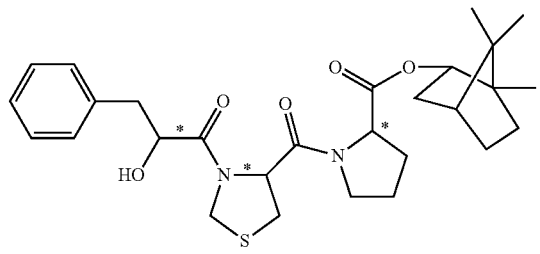 |
| 221S-91 | 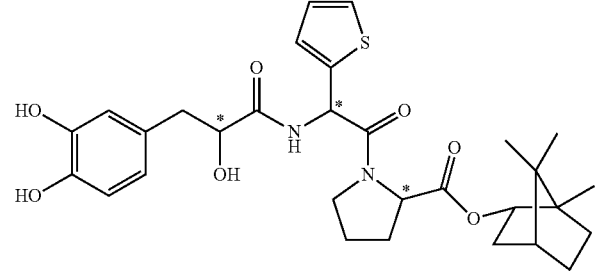 |
| 221S-92 | 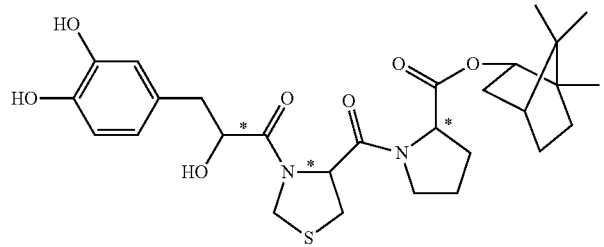 |

-continued

| No. | formula |
|---|---|
| 221S-93 | |
| 221S-94 | |
| 221S-95 | |
| 221S-96 | |
| 221S-97 | |
| 221S-98 | |

-continued

| No. | formula |
|---|---|
| 221S-99 | |
| 221S-100 | |
| 221S-101 | |
| 221S-102 | |

| No. | formula |
|---|---|
| 221S-103 | |
| 221S-104 | |
| 221S-105 | |
| 221S-106 | |

| No. | formula |
|---|---|
| 221S-107 | |
| 221S-108 | |
| 221S-109 | |
| 221S-110 | |
| 221S-111 | |

| No. | formula |
|---|---|
| 221S-112 | 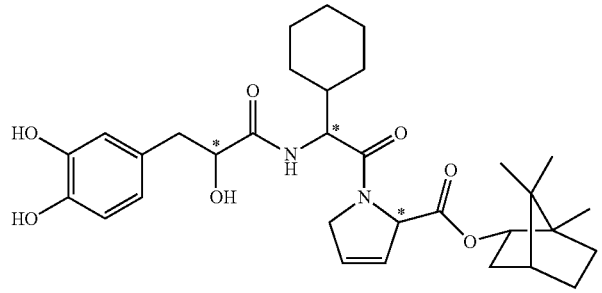 |
| 221S-113 | 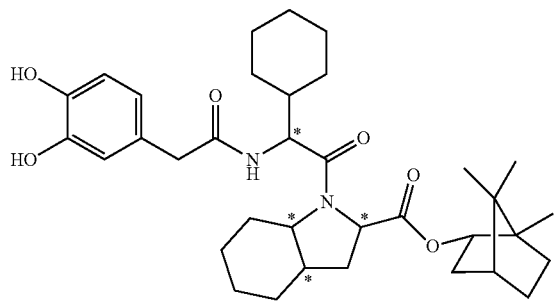 |
| 221S-114 | 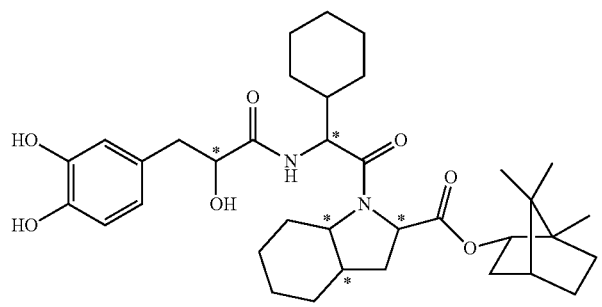 |
| 221S-115 | 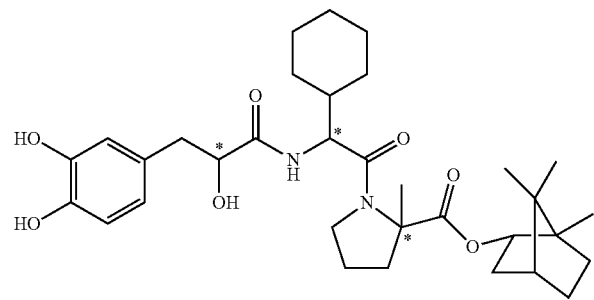 |
| 221S-116 | 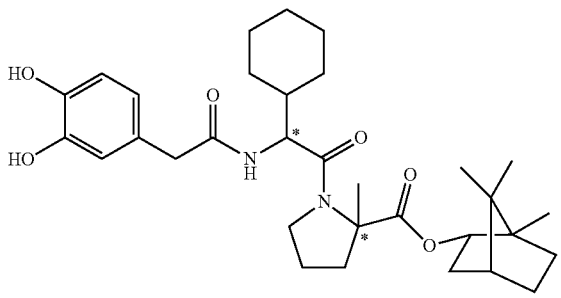 |

-continued

| No. | formula |
|---|---|
| 221S-117 | |
| 221S-118 | |
| 221S-119 | |
| 221S-120 | |
| 221S-121 | |
| 221S-122 | |

-continued

| No. | formula |
|---|---|
| 221S-123 | |
| 221S-124 | |
| 221S-125 | |
| 221S-126 | |
| 221S-127 | |
| 221S-128 | |

| No. | formula |
|---|---|
| 221S-129 | |
| 221S-130 | |
| 221S-131 | |
| 221S-132 | |
| 221S-133 | |

-continued
| No. | formula |
|---|---|
| 221S-134 | 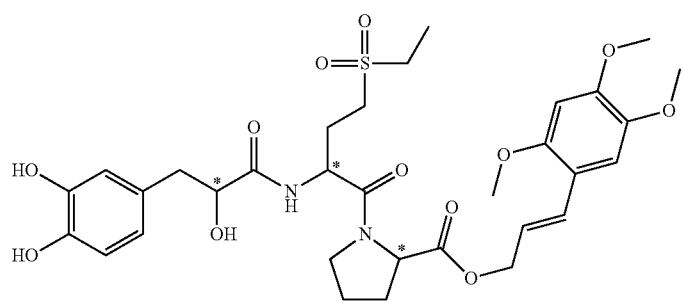 |
| 221S-135 | 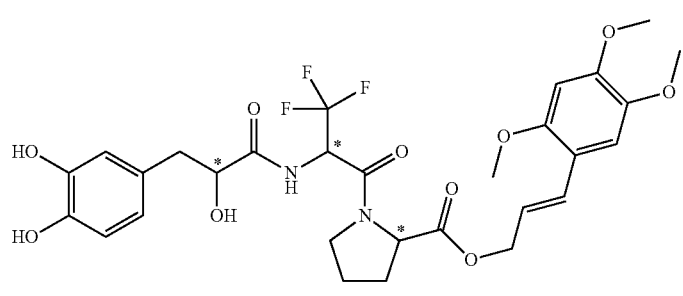 |
| 221S-136 | 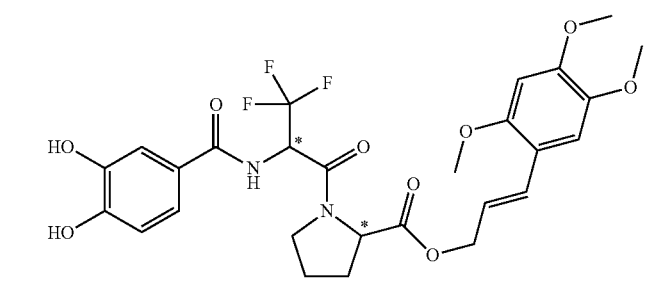 |
| 221S-137 | 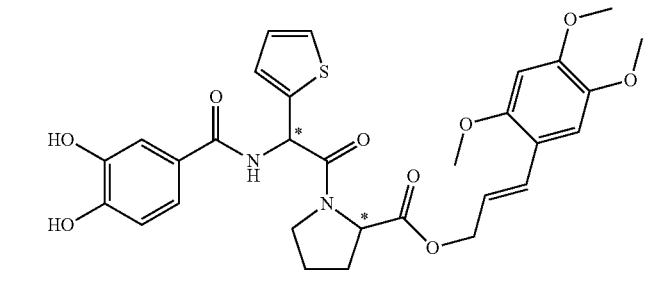 |
| 221S-138 | 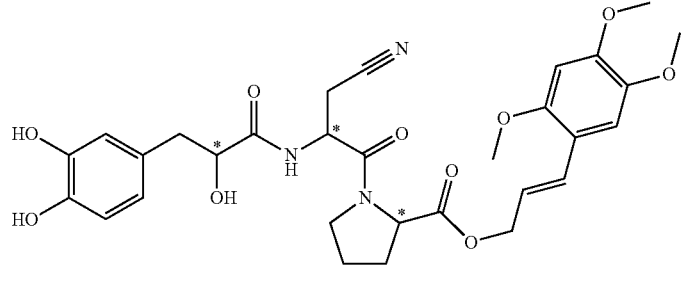 |

-continued

| No. | formula |
|---|---|
| 221S-139 | |
| 221S-140 | |
| 221S-141 | |
| 221S-142 | |
| 221S-143 | |

| No. | formula |
|---|---|
| 221S-144 | |
| 221S-145 | |
| 221S-146 | |
| 221S-147 | |
| 221S-148 | |
| 221S-149 | |
| 221S-150 | |

| No. | formula |
|---|---|
| 221S-151 | |
| 221S-152 | |
| 221S-153 | |
| 221S-154 | |
| 221S-155 | |
| 221S-156 | |
| 221S-157 | |
| 221S-158 | |

| No. | formula |
|---|---|
| 221S-159 |  |
| 221S-160 |  |
| 221S-161 |  |
| 221S-162 |  |
| 221S-163 |  |
| 221S-164 |  |

-continued

| No. | formula |
|---|---|
| 221S-165 | |
| 221S-166 | |
| 221S-167 | |
| 221S-168 | |
| 221S-169 | |
| 221S-170 | |
| 221S-171 | |
| 221S-172 | |

-continued

| No. | formula |
|---|---|
| 221S-173 | |
| 221S-174 | |
| 221S-175 | |
| 221S-176 | |
| 221S-177 | |
| 221S-178 | |
| 221S-179 | |

-continued

| No. | formula |
|---|---|
| 221S-180 | |
| 221S-181 | |
| 221S-182 | |
| 221S-183 | |
| 221S-184 | |
| 221S-185 | |
| 221S-186 | |

-continued
| No. | formula |
|---|---|
| 221S-187 | 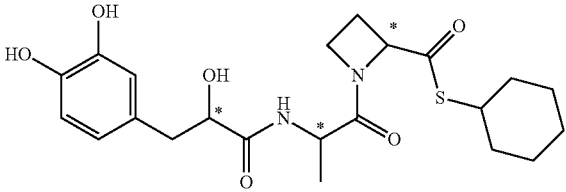 |
| 221S-188 | 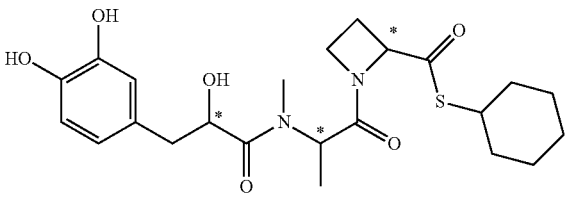 |
| 221S-189 | 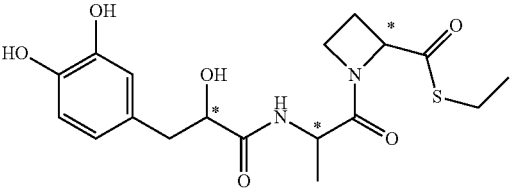 |
| 221S-190 | 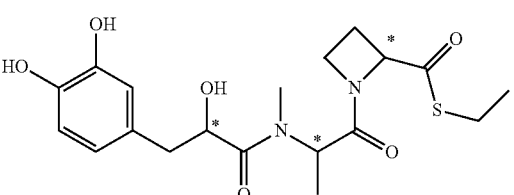 |
| 221S-191 | 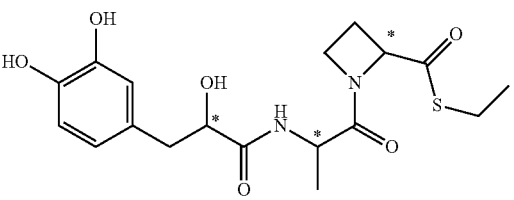 |
| 221S-192 | 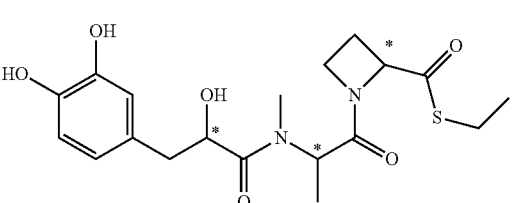 |
| 221S-193 | 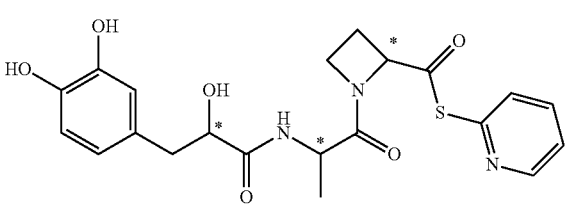 |

-continued

| No. | formula |
|---|---|
| 221S-194 | |
| 221S-195 | |
| 221S-196 | |
| 221S-197 | |
| 221S-198 | |
| 221S-199 | |
| 221S-200 | |

-continued

| No. | formula |
|---|---|
| 221S-201 | |
| 221S-202 | |
| 221S-203 | |
| 221S-204 | |
| 221S-205 | |
| 221S-206 | |
| 221S-207 | |

| No. | formula |
|---|---|
| 221S-208 | |
| 221S-209 | |
| 221S-210 | |
| 221S-221 | | wherein, "*" represents a chiral center, and the compound comprising "*" includes all chiral isomers of the structural formula.

The present invention also provides a hydrolyzate of the compound above wherein Y is oxygen.

The present invention also provides an enantiomer, tautomer, stereoisomer, rotamer, diastereomer or racemate of the compound above.

The present invention also provides a pharmaceutically acceptable salt and a pharmaceutically acceptable ester of the compound above, wherein the pharmaceutically acceptable salt includes pharmaceutically acceptable acid salt and pharmaceutically acceptable basic salt, wherein the pharmaceutically acceptable acid salt includes a salt formed with one of the following acids: sulfuric acid, hydrogen sulfate, hydrochloric acid, hydrobromic acid, phosphoric acid, nitric acid, carbonic acid, boric acid, methanesulfonic acid, benzenesulfonic acid, p-toluenesulfonic acid, formic acid, acetic acid, propionic acid, butyric acid, pyruvic acid, maleic acid, malic acid, tartaric acid, citric acid, ascorbic acid, benzoic acid, camphoric acid, fumaric acid, oxalic acid, succinic acid, camphorsulfonic acid, maleic acid, salicylic acid or α-lactic acid; the pharmaceutically acceptable basic salt includes a salt formed by one of the following bases: alkali metals including lithium, sodium and potassium; alkaline earth metals including magnesium, and calcium; lithium hydroxide, sodium hydroxide, potassium hydroxide, lithium hydride, sodium hydride, butyllithium, ammonium, triethylamine, diisopropylethylamine, ornithine, arginine, lysine or histidine; and the pharmaceutically acceptable ester includes an ester formed through a hydroxyl group or a phenolic hydroxyl group in the compound with an acid.

The present invention also provides a solvated mixture of the compound above, wherein the solvate is one selected from water, methanol, ethanol, isopropanol, butanol, ethyl acetate and DMSO, or a combination thereof.

The present invention also provides a method for preparing the compound mentioned above, where the method comprises:

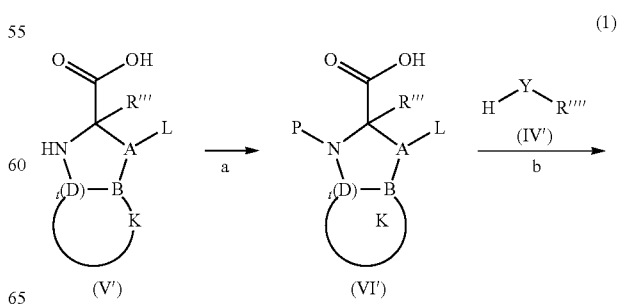

(1)

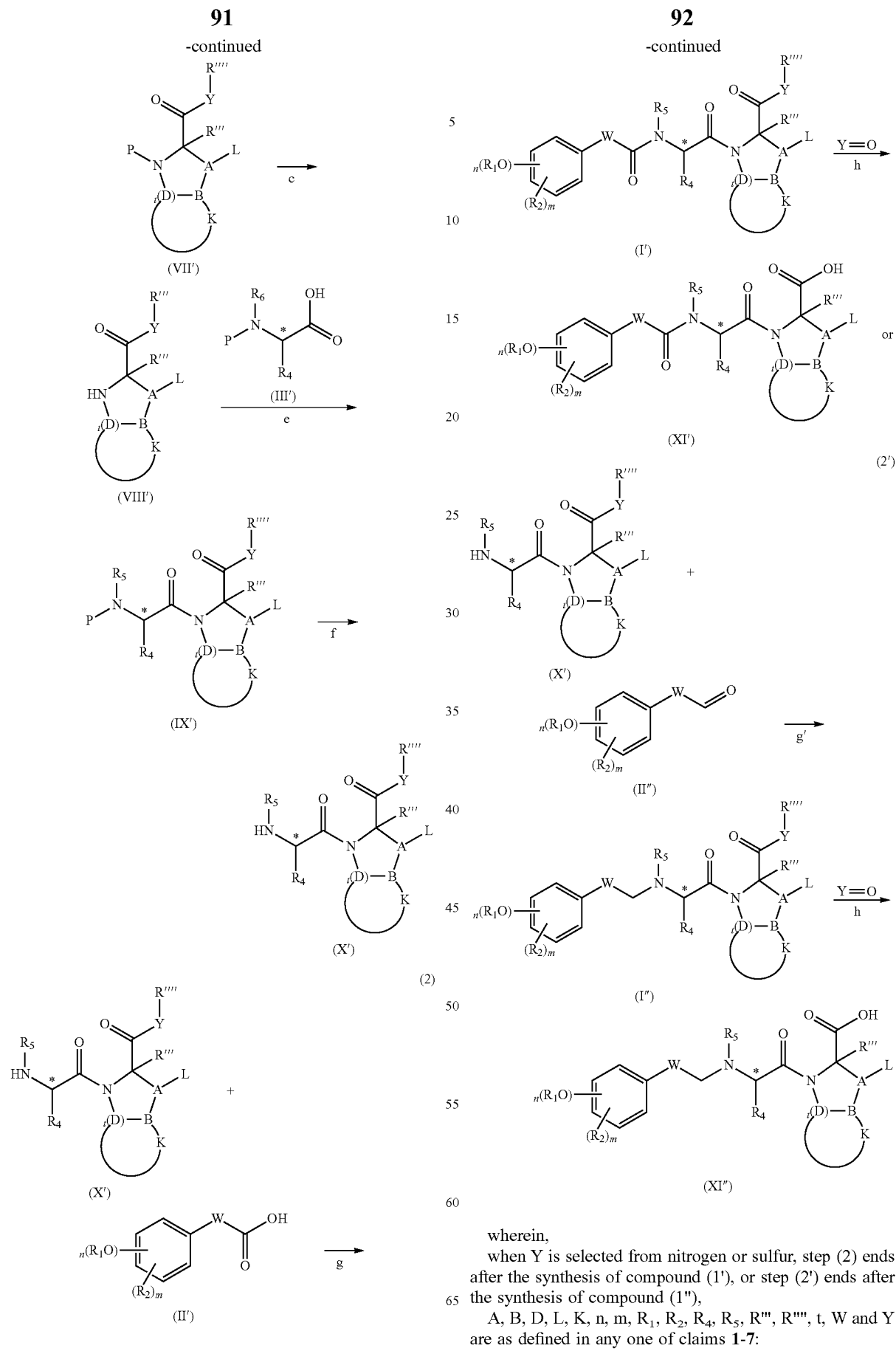
wherein,
when Y is selected from nitrogen or sulfur, step (2) ends after the synthesis of compound (1'), or step (2') ends after the synthesis of compound (1"),
A, B, D, L, K, n, m, $R_1$, $R_2$, $R_4$, $R_5$, R''', R'''', t, W and Y are as defined in any one of claims 1-7:

a: protection of the amino of α-amino acid; P represents a suitable protecting group and is selected from tert-butoxycarbonyl(Boc), allyloxycarbonyl(Alloc), benzyloxycarbonyl, trityl, benzyloxymethyl, fluorenylmethoxycarbonyl (Fmoc), phthaloyl, dithiosuccinyl, methoxyformyl, ethoxyformyl, benzenesulfonyl, p-toluenesulfonyl, 2-(trimethylsilyl) ethanesulfonyl, benzyl(Bn), trityl(Tr) or allyl;

b: conditions for synthesis of peptide bond;
c: deprotection corresponding to step a;
e: the same as b:
f: the same as c;
g: the same as b;
g': reductive amination;
h: conditions for ester hydrolysis;
wherein, "*" represents a chiral center, and the compound comprising "*" includes all chiral isomers of the structural formula.

On the other aspect, the present invention provides use of the compound mentioned above in the manufacture of a medicament for the prophylaxis, treatment or delay of hypertension and its complications, wherein the complications include one or more of coronary heart disease, angina pectoris, acute heart failure, chronic congestive heart failure, myocardial infarction and sequelae, congestive heart disease, myocardial ischemia, myocarditis, myocardial fibrosis, myocardial hypertrophy, atherosclerosis, benign small arterial nephrosclerosis, malignant small arterial nephrosclerosis, vascular growth abnormality and remodeling, angiogenesis-related diseases (such as new vascular macular degeneration), hyperaldosteronism, arrhythmia, kidney disease, diabetes, stroke, thrombosis, renal failure (such as diabetic nephropathy), hyperlipidemia, obesity, hyperglycemia, retinal arteriosclerosis, and hypertensive fundus lesions.

On the other aspect, the present invention provides a pharmaceutical composition comprising: the compound mentioned above, a pharmaceutically acceptable salt of the compound according to any one of claims 1 to 8, a pharmaceutically acceptable carrier, excipient and diluent of the compound mentioned above.

On the other aspect, the present invention provides use of the above pharmaceutical composition in the manufacture of a medicament for the prophylaxis, treatment or delay of hypertension and its complications, wherein the complications include one or more of coronary heart disease, angina pectoris, heart failure (acute or chronic congestive heart failure), myocardial infarction and sequelae, congestive heart disease, myocardial ischemia, myocarditis, myocardial fibrosis, myocardial hypertrophy, atherosclerosis, benign small arterial nephrosclerosis, malignant small arterial nephrosclerosis, vascular growth abnormality and remodeling angiogenesis-related diseases (such as new vascular macular degeneration), hperaldosteronism, arrhythmia, kidney disease, diabetes, stroke, thrombosis, renal failure (eg, diabetic nephropathy), hyperlipidemia, obesity, hyperglycemia, retinal arteriosclerosis, and hypertensive fundus lesions.

The compound involved in the present invention has an effect of inhibiting the biological activity of angiotensin converting enzyme, and itself and its pharmaceutical composition has prevention and treatment effect on hypertension and other cardiovascular and cerebrovascular diseases.

DETAILED DESCRIPTION OF EMBODIMENTS

Figure 1:
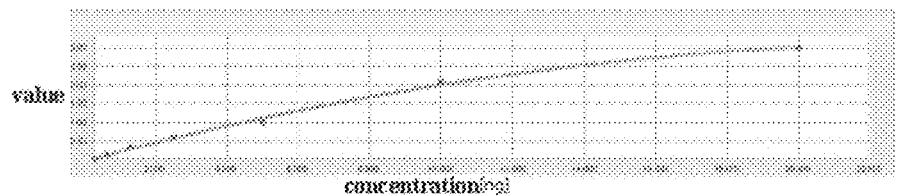
FIG. 1 is a quadratic curve fitting chart between the concentration of angiotensin converting enzyme and the value of OD 450 nm.

Danshen (Latin name: *Salvia miltiorrhiza* Bunge), as a member of traditional Chinese medicines, has been used in the treatment of cardiovascular and cerebrovascular diseases. Recently, in the treatment of hypertension, the synergistic effect of danshen has been reported in many literatures. (*Biological & Pharmaceutical Bulletin,* 2011, 34 (10), 1596-1601; *Phytotherapy Research,* 2010, 24(5), 769-774; *American Journal of Physiology,* 2007, 292(5, Pt. 2), H2131-H2137; *Chinese Journal of Clinical Rehabilitation,* 2006, 10(23), 73-75; *Medicinal and Aromatic Plants—Industrial Profiles,* 2000, 14(Sage), 193-205). In combination with the pril and sartan antihypertensive drugs, danshen drugs have significant clinical effect, especially in patients with hypertension associated with diabetes.

Danshensu is the main ingredient of the water soluble extract of danshen, and its catechol and lactic acid structure impart it unique effects of antioxidant, cardiovascular protection, vasodilatation promoting, blood pressure reducing and the like (Characterization of the Radical Scavenging and Antioxidant Activities of Danshensu and Salvianolic Acid B. *Food and Chemical Toxicology* 2008, 46(1), 73-81; Protective effect of danshensu on endothelial vascular activity in rats with isoproterenol-induced injury and its mechanism. *Chinese herbal medicine,* 2013, 1: 59-64). It has been found that polyphenolic natural products have inhibitory effects on angiotensin converting enzyme. (Angiotensin-Converting Enzyme Inhibitory Effects by Plant Phenolic Compounds: A Study of Structure Activity Relationships. *J. Agric. Food Chem.* 2013, 61, 11832-11839; Inhibition of Angiotensin-Converting Enzyme by Quercetin Alters the Vascular Response to Brandykinin and Angiotensin I. *Pharmacology,* 2002, 65, 182-186; Ferulic Acid Improves Cardiovascular and Kidney Structure and Function in Hypertensive Rats. *J. Cardiovasc. Pharmacol.* 2013, 61, 240-249; Tannic Acid, an Inhibitor for Renal Angiotensin Type 1 Receptor and Hypertension in Spontaneously Hypertensive Rats. *Endocr Rev.* 2012, 33, SAT-248.) The present invention, by reference to the results of the previous research (CN 1868998A, borneol β-(3,4-dihydroxyphenyl)-α-hydroxypropionate, its synthesis method and use), introduces the danshensu group and other phenolic groups into the skeletal of the molecules of traditional ACE drugs, and at the same time introduces borneol, menthol and other groups according to the ideas of "monarch drug-conductant drug pair" and prodrug design, and thus a new class of drugs with activity for angiotensin converting enzyme inhibition have been designed.

The present invention makes reference to the chemical structures of the disclosed angiotensin converting enzyme inhibitors such as captopril, enalapril, lisinopril, perindopril, alacepril, delapril, quinapril, ramipril, cilazapril, benazepril, fosinopril, zofenopril, trandolapril, imidapril, temocapril, spirapril and moexipril.

The present invention also makes reference to the patent literatures on angiotensin converting enzyme inhibitors, such as Antihypertensive mercaptoacylamino acid derivatives and their use, (1980, EP 9898 A1), Preparation of converting enzyme inhibitor 5,6-dihydro[1,4]thiazino[4,3-a]quinoline-(2H), 4(4aH)-dione, (1981, U.S. Pat. No. 4,273,927 A). [4R]-3-(ω-Aroylpropionyl)-4-thiazolidinecarboxylic acids and esters, (1983, U.S. Pat. No. 4,374,249 A).

The present invention also makes reference to WO 9302679 A1 (1993), Method of treating premenstrual syndrome by administration of an angiotensin-converting enzyme inhibitor, which discloses the following compound:

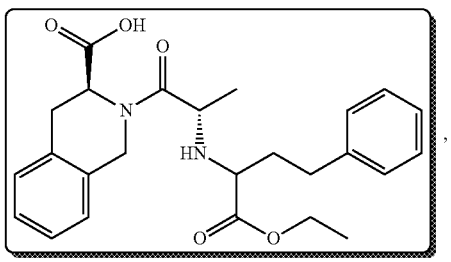

The present invention also makes reference to US 20070032661 A1 (2007), Process for the preparation of intermediates of perindopril, which discloses the following compounds:

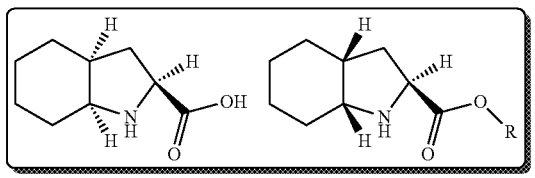

In the full text of the present invention, unless otherwise indicated, the following definitions of names or terms apply to all aspects of the present invention.

The term "alkyl" means a straight or branched aliphatic hydrocarbon group containing from 1 to 15 carbon atoms, preferably from 1 to 6 carbon atoms, including, but not limited to, methyl, ethyl, propyl, and isopropyl.

The term "substituted alkyl" means the alkyl group substituted with one or more substituents, which may be the same or different, and each independently selected from the group consisting of alkyl, cycloalkyl, aryl, cyano, nitro, halo, alkoxy, amino, alkyl-substituted primary, secondary, or tertiary amino or cycloalkyl-substituted primary, secondary, or tertiary amino, hydroxy, mercapto, alkylthio, alkylketo, and carboxyl.

The term "alkenyl" refers to a straight or branched or cyclic aliphatic hydrocarbon radical containing at least one C=C double bond and 2 to 15 carbon atoms, preferably from 2 to 8 carbon atoms.

The term "substituted alkenyl" refers to the alkenyl group substituted with one or more substituents, which may be the same or different, and each independently selected from the group consisting of alkyl, cycloalkyl, aryl, cyano, nitro, halo, alkoxy, amino, alkyl-substituted primary, secondary or tertiary amino or cycloalkyl-substituted primary, secondary, or tertiary amino, hydroxy, mercapto, alkylthio, alkylketo, and carboxyl.

The term "alkynyl" refers to a straight or branched or cyclic aliphatic hydrocarbon radical containing at least one C≡C double bond and 2 to 15 carbon atoms, preferably from 2 to 8 carbon atoms.

The term "substituted alkynyl" refers to the alkynyl group substituted with one or more substituents, which may be the same or different, and each independently selected from the group consisting of alkyl, cycloalkyl, aryl, cyano, nitro, halo, alkoxy, amino, alkyl-substituted primary, secondary, or tertiary amino or cycloalkyl-substituted primary, secondary, or tertiary amino, hydroxy, mercapto, alkylthio, alkylketo, and carboxyl.

The term "aryl" refers to an aromatic monocyclic or polycyclic structure comprising 6 to 14 carbon atoms, preferably 6 to 12 carbon atoms.

The term "substituted aryl" refers to the aryl group substituted with one or more substituents, which may be the same or different, and each independently selected from the group consisting of alkyl, cycloalkyl, aryl, cyano, nitro, halo, alkoxy, amino, alkyl-substituted primary, secondary, or tertiary amino or cycloalkyl-substituted primary, secondary, or tertiary amino, hydroxy; mercapto, alkylthio, alkylketo, and carboxyl.

The term "heteroaryl" refers to an aromatic monocyclic or polycyclic structure comprising 5 to 14 carbon atoms, preferably 5 to 12 carbon atoms, in which one or more carbon atoms of the rings is substituted with other elements including, but not limited to, nitrogen, oxygen, and sulfur. Preferred heteroaryl groups include, but are not limited to, pyridinyl, pyrimidinyl, pyrazinyl, pyridazinyl, indolyl, quinolyl, isoquinolyl, pyrazolyl, furyl, thienyl, thiazolyl, oxazolyl, pyrrolyl, benzofuranyl, and benzothienyl.

The term "substituted heteroaryl" refers to the heteroaryl group substituted with one or more substituents, which may be the same or different, and each independently selected from the group consisting of alkyl, cycloalkyl, aryl, cyano, nitro, halo, alkoxy, amino, alkyl-substituted primary, secondary, or tertiary amino or cycloalkyl-substituted primary, secondary, or tertiary amino, hydroxy, mercapto, alkylthio, alkylketo, and carboxyl. Preferred substituted aralkyl groups include, but are not limited to, tetramethylpyrazine alcohol group.

The term "aralkyl" means an aryl-alkyl group, in which the aryl and alkyl are as described above. Preferred aralkyl groups include, but are not limited to, benzyl and phenethyl.

The term "substituted aralkyl" refers to the aralkyl group substituted with one or more substituents, which may be the same or different, and each independently selected from the group consisting of alkyl, cycloalkyl, aryl, cyano, nitro, halo, alkoxy, amino, alkyl-substituted primary, secondary, or tertiary amino or cycloalkyl-substituted primary, secondary, or tertiary amino, hydroxy, mercapto, alkylthio, alkylketo, and carboxyl. Preferred substituted aralkyl groups include, but are not limited to, p-methylbenzyl and *asarum* alcohol group.

The term "cycloalkyl" refers to non-aromatic monocyclic or polycyclic structure, typically containing from 3 to 10 carbon atoms, preferably from 3 to 7 carbon atoms, including, but not limited to, cyclopropyl, cyclobutyl, cyclopentyl, cyclohexyl and cycloheptyl.

The term "substituted cycloalkyl" refers to the cycloalkyl group substituted with one or more substituents, which may be the same or different, and each independently selected from the group consisting of alkyl, cycloalkyl, aryl, cyano, nitro, halo, alkoxy, amino, alkyl-substituted primary, secondary, or tertiary amino or cycloalkyl-substituted primary, secondary, or tertiary amino, hydroxy, mercapto, alkylthio, alkylketo, and carboxyl. Preferred substituted cycloalkyl group comprises 3-7 carbon atoms, including, but not limited to, dextrobornyl, levomenthol and norbornyl.

The term "halogen" means fluorine, chlorine, bromine, and iodine. Preferred halogens include fluorine, chlorine and bromine.

The term "heterocyclyl" means a non-aromatic saturated monocyclic or polycyclic ring system, generally containing 10 or less ring atoms, and preferably 4 to 10 ring atoms, and containing one or more non-carbon atoms, such as nitrogen, oxygen, sulfur atoms, which may be present alone or in combination, wherein no adjacent oxygen-oxygen, oxygen-sulfur or sulfur-sulfur groups is present in the ring system. Preferred heterocyclyl groups include, but are not limited to, piperazinyl, morpholinyl, thiomorpholinyl, piperidinyl, pyrrolyl and the like.

The term "substituted heterocyclyl" refers to the heterocyclyl group substituted with one or more substituents, which may be the same or different, and each independently selected from the group consisting of alkyl, cycloalkyl, aryl, cyano, nitro, halo, alkoxy, amino, alkyl-substituted primary, secondary, or tertiary amino or cycloalkyl-substituted primary, secondary, or tertiary amino, hydroxy, mercapto, alkylthio, alkylketo, and carboxyl. Preferred substituted heterocyclyl groups include, but are not limited to, N-methylpiperazinyl, 3-fluoropiperidinyl, 2,6-dimethylmorpholinyl, 2-methylpyrrolyl and the like.

The term "heteroarylalkyl" refers to a heteroaryl-alkyl group, in which heteroaryl and alkyl are as described above. Preferred heteroarylalkyl groups include, but are not limited to, 2-pyridylmethyl, 3-pyridylmethyl and 4-pyridylmethyl.

The term "acyl" refers to alkyl-C(O)—, substituted alkyl-C(O)—, cycloalkyl-C(O)—, substituted cycloalkyl-C(O)—, and heterocyclyl-C(O)—, in which each group is as described above. Preferred acyl groups include, but are not limited to, acetyl, propionyl and cyclobutanoyl.

The term "aroyl" refers to aryl-C(O)—, and substituted aryl-C(O)—, in which each group is as described above. Preferred aroyl groups include, but are not limited to, benzoyl and p-methylbenzoyl.

The term "alkoxy" refers to alkyl-O— and substituted alkyl-O—, in which each group is as described above. Preferred alkoxy groups include, but are not limited to, methoxy, ethoxy, isopropyl, dextrobornyloxy, levomentholoxy, 2,3,4-trimethoxybenzene-2'-allyloxy (asary-alcohol oxy group) and tetramethylpyrazine oxy group.

The term "aralkyloxy" refers to aralkyl-O— and substituted aralkyl-O—, in which each group is as described above. Preferred aralkyloxy groups include, but are not limited to, benzyloxy, and, 3,4-trimethoxybenzene-2'-allyloxy (asary-alcohol oxy group).

The term "aryloxy" refers to aryl-O— and substituted aryl-O—, in which each group is as described above. Preferred aryloxy groups include, but are not limited to, phenoxy and p-methylphenoxy.

The term "alkylthio" refers to alkyl-S— group, in which the alkyl moiety is as described above. Preferred alkylthio groups include, but are not limited to, methylthio, ethylthio and propylthio.

The term "aralkylthio" refers to aralkyl-S— group, in which the "aralkyl moiety is as described above. Preferred aralkylthio groups include, but are not limited to, phenylmethylthio and phenylethylthio.

The term "arylthio" refers to aryl-S— group, in which the aryl group is as described above. Preferred arylthio groups include, but are not limited to, phenylthio.

The term "alkylsulfonyl" refers to alkyl-S($O_2$)— group, in which the alkyl is as described above. Preferred alkylsulfonyl groups include, but are not limited to, methylsulfonyl, and ethylsulfonyl.

The term "arylsulfonyl" refers to aryl-S($O_2$)— group, in which the aryl is as described above. Preferred arylsulfonyl groups include, but are not limited to, benzenesulfonyl and naphthylsulfonyl.

The term "at least one" means one or more.

The term "substituted" means that designated groups replaces one or more hydrogens on a specified atom while meeting the normal valence of the specified atom and resulting a stable compound.

The term "optionally substituted" means selecting a specified group, radical, or portion to substitute.

3. Salt and Solvate

The tripeptides and analogs thereof designed in the present invention also include "prodrugs", "solvates", "salts" (including "acid salts", "basic salts" and internal salts) and "esters" thereof. The "prodrugs". "solvates", "salts" and "esters" of the tripeptides are all within the scope of the present invention. The "solvate" and "salt" are equivalent to the free form of the corresponding compound.

The term "prodrug" refers to a precursor compound of a drug which can be metabolized or in vivo chemically converted into the compound of formula (I) or a salt, a solvate thereof or an ester thereof.

The term "solvate" means that the compound of the present invention is physically associated with one or more solvent molecules. The physical association involves various degrees of ionic and covalent bonding, including hydrogen bonding, van der Waals force and so on. The "solvate" consists of two parts: the solution phase and the separable solvate. Suitable solvates include, but are not limited to, hydrates, methanolates, ethanolates, DMSO solvate and ethyl acetate solvate.

The term "salt" includes acid salts, basic salts and internal salts, and means acid salts formed by the tripeptide compounds (formula (I)) designed in the present invention with inorganic acids or organic acids, basic salts formed by with inorganic bases and organic bases, and internal salts formed by the basic groups (such as an amino group, a guanidino group, an imidazolyl group, or an indolyl group, etc.) contained in the tripeptide compounds (formula (I)) and the acid groups (such as a carboxylate, alkyl sulfonate, or phosphate, etc.).

The acids used for forming the acid salt includes but is not limited to the following acids:

sulfuric acid, hydrogen sulfate, hydrochloric acid, hydrobromic acid, phosphoric acid, nitric acid, carbonic acid, boric acid, methanesulfonic acid, benzenesulfonic acid, p-toluenesulfonic acid, formic acid, acetic acid, propionic acid, butyric acid, pvruvic acid, maleic acid, malic acid, tartaric acid, citric acid, ascorbic acid, benzoic acid, camphoric acid, fumaric acid, oxalic acid, succinic acid, camphorsulfonic acid, maleic acid, salicylic acid and α-lactic acid. In addition, the pharmaceutically acceptable salt-forming acids described in P. Stahl, Camille G. eds. *Handbook of Pharmaceutical Salts. Properties, Selection and Use,* 2002, Zurich: Wiley-VCH are incorporated herein by reference.

The base used for forming the basic salt includes, but is not limited to, the following bases:

alkali metals such as lithium, sodium and potassium; alkaline earth metals such as magnesium and calcium; lithium hydroxide, sodium hydroxide, potassium hydroxide, lithium hydride, sodium hydride, butyllithium, ammonium, triethylamine, diisopropylethylamine, basic amino acids such as ornithine, arginine, lysine or histidine.

In addition, the pharmaceutically acceptable ester formed by the tripeptide compound of the present invention means a carboxylate ester formed from a hydroxyl group or a phenolic hydroxyl group in the compound and a carboxylic acid (including but not limited to: alkyl carboxylic acid, substituted alkyl carboxylic acid, aryl carboxylic acid, substituted aryl carboxylic acid, aralkyl carboxylic acid, substituted aralkyl carboxylic acid, cycloalkyl carboxylic acid, substituted cycloalkyl carboxylic acid, heterocyclic carboxylic acid and heteroarylalkyl carboxylic acid, such as acetate, propionate, benzoate, and nicotinate); a sulfonate ester formed from a hydroxyl group or a phenolic hydroxyl group in the compound and a sulfonic acid (including but not limited to: alkyl sulfonic acid, aryl sulfonic acid and substituted aryl sulfonic acid ester, such as methanesulfonate, benzenesulfonate, p-toluenesulfonate); and an ester formed from a hydroxyl group or a phenolic hydroxyl group in the compound and an amino acid (including but not limited to: α-amino acid, β-amino acid, ω-amino acid, such as alanine esters and glutamate esters); and a phosphate ester formed from a hydroxyl group or a phenolic hydroxyl group in the compound and a phosphoric acid, monoalkyl phosphoric acid, dialkyl phosphoric acid, phosphorous acid (such as, diethyl phosphite).

In addition, the tripeptide compounds of the present invention and pharmaceutically acceptable (non-toxic, physiologically acceptable) "solvates", "salts" (including "acid salts", "basic salts" and internal salts), "esters", related "prodrugs", and the involved enantiomers, stereoisomers, rotamers, tautomers, positional isomers and racemates are within the scope of the present invention.

In addition, it is possible to protect the sensitive or reactive groups on the molecules of interest in the synthesis process. Representative protecting groups are described in T. W. Greene and P. G. M. Wuts "Protective Groups in Organic Synthesis" John Wiley & Sons, Inc., New York, 1999, the entire contents of which are incorporated herein by reference. The corresponding protecting groups can be added or removed using methods well known in the art.

4. Pharmaceutical Composition

The term "composition" refers to a product comprising a specific amount of a particular ingredient, and any product that is directly or indirectly formed by combination of specific amounts of particular ingredients.

"Mammal" means humans and other mammals.

"Patients" includes people and animals.

The term "effective amount" means that the amount of the compound or pharmaceutical composition described herein is effective in inhibiting angiotensin converting enzyme and thus produces the desired effect of prophylaxis, treatment, amelioration or inhibition.

The term "pharmaceutically acceptable carrier" refers to a compound and compositions having sufficient purity and quality for formulating the composition of the present invention, which does not produce an adverse reaction and acts as a pharmaceutical carrier when administered to an animal.

The term "pharmaceutically acceptable diluent" refers to a compound and compositions having sufficient purity and quality for formulating the composition of the present invention, which does not produce an adverse reaction and acts as a pharmaceutical diluent when administered to an animal.

Pharmaceutical compositions generally comprise at least one compound of the invention and one or more pharmaceutically acceptable carriers. Solid dosage forms can comprise: fillers (such as starch, microcrystalline cellulose, sucrose, glucose, lactose, sorbitol, mannitol, etc.), binders (gelatin, carboxymethylcellulose, alginate, gum acacia), humectants (glycerol), disintegrating agents (calcium carbonate, starch, agar, alginic acid), dissolution retardants (paraffin), absorption accelerators (quaternary ammonium compounds), wetting agents (cetyl alcohol, glyceryl monostearate), adsorbents (kaolin, bentonite), lubricants (talc; solid polyethylene glycol; potassium, calcium or magnesium salt of state; lauryl sulfate; water-soluble lubricants including sodium chloride, sodium acetate, sodium benzoate sodium oleate, colorants (clay, alumina) and buffers.

The compounds of the present invention may be formulated into suitable dosage forms, such as tablets and capsules, in accordance with conventional pharmaceutical processes.

5. Disorders and Diseases

The compounds (I) of the present invention and pharmaceutically acceptable (non-toxic, physiologically acceptable) salts, esters and pharmaceutical compositions are useful for the prevention, treatment or delay of cardiovascular and cerebrovascular diseases, particularly those associated with hypertension and complication thereof.

The disorders and disease include one or more of hypertension, coronary heart disease, angina pectoris, heart failure (acute or chronic congestive heart failure), myocardial infarction and sequelae, congestive heart disease, myocardial ischemia, myocarditis, cardiac fibrosis, myocardial hypertrophy, atherosclerosis, benign small arterial nephrosclerosis, malignant small arterial nephrosclerosis, vascular growth abnormalities and remodeling, angiogenesis-related diseases (such as new vascular macular degeneration), hyperaldosteronism, arrhythmia, kidney disease, diabetes, stroke, thrombosis, renal failure (such as diabetic nephropathy), hyperlipidemia, obesity, hyperglycemia, retinal arteriosclerosis, and hypertensive fundus lesions.

6. The method for preparation of *asarum* alcohol involved in the present invention comprises:

(1) reacting compound V with compound VI in the presence of a fatty alcohol and a catalyst to give compound VII:

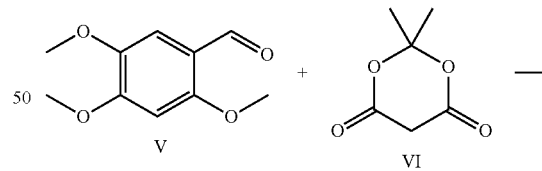

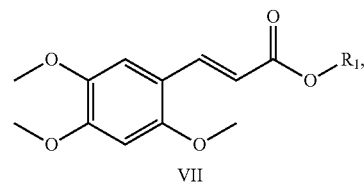

wherein R₁ is selected from a linear or branched $C_1$-$C_5$ alkyl; and (2) reducing compound VII to give compound VIII;

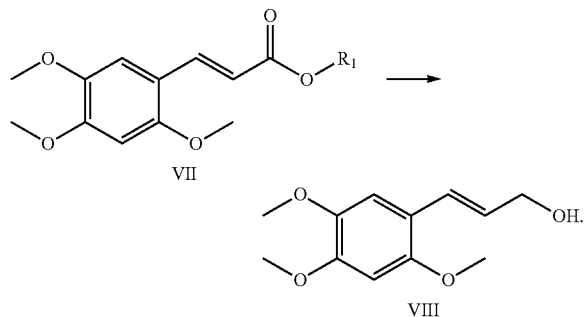

In step (1), compound VI is reacted with aliphatic alcohol in xylene, toluene or benzene under reflux for 3-12 hours, and preferably for 4-10 hours. After cooling to room temperature, 2,4,5-trimethoxybenzaldehyde (compound V) and catalyst are added to the reaction mixture, and the mixture is further refluxed for 5-24 hours and preferably for 8-14 hours to give compound VII. The aliphatic alcohol used in step (1) is one of methanol, ethanol, propanol, isopropanol, butanol, isobutanol, n-amyl alcohol and isoamyl alcohol, or any combination thereof, and preferably one of methanol and ethanol, or any combination thereof. The molar ratio of the aliphatic alcohol to compound VI is 1:1 to 1:10, and preferably the molar ratio of the aliphatic alcohol to compound VI is 1:1 to 1:4. The catalyst used is one of pyridine, 2,4,6-trimethylpyridine, 2,6-dimethylpyridine, 2,6-di-tert-butyl-4-methylpyridine, 4-dimethylpyridine, piperidine and tetrahydropyrrole, or any combination thereof. The molar ratio of the catalyst to 2,4,5-trimethoxybenzaldehyde is 0.1:1 to 2:1.

In step 2, the reducing agent used is sodium borohydride, sodium dihydro-bis(2-methoxyethoxy) aluminate, lithium aluminum hydride or diisobutylaluminum hydride, and the molar ratio of the reducing agent to compound VII is 1:1 to 10:1. The solvent used is one of tetrahydrofuran, 1,4-dioxane, dimethylethyl ether, toluene, benzene, xylene, diethyl ether, methyl tert-butyl ether, dichloromethane, dichloroethane, trichloromethane, tetrachloromethane and n-hexane or any combination thereof. The reaction temperature is between 78° C. and 25° C.; and the reaction time is between 0.5 and 24 hours.

Abbreviations

EDCI 1-ethyl-(3-dimethylaminopropyl)carbodiimide hydrochloride
DCC Dicyclohexylcarbodiimide
Alloc Allyloxycarbonyl
Fmoc Fluorenylmethoxycarbonyl
Bn Benzyltrityl
Tr Trityl
T3P® 1-propylphosphoric anhydride
HOBt 1-hydroxybenzotriazole
THF Tetrahydrofuran
EtOAc Ethyl acetate
MeOH Methanol
EtOH Ethanol
TFA Trifluoroacetic acid
DCM Dichloromethane
DIPEA Diisopropylethylamine
DMF N,N-dimethyl acetamide
DMSO Dimethyl sulfoxide
DMAP 4-N,N-dimethylpyridine
HATU 2-(7-azobenzotriazole)-N,N,N',N'-tetramethyluronium hexafluorophosphate
PyBOP 1H-benzotriazol-1-yloxytripyrrolidyl hexafluorophosphate
Boc tert-butoxycarbonyl
Cbz Benzyloxycarbonyl
NMR nuclear magnetic resonance
MS mass spectrometry Hereinafter, specific preparation and examples of the present invention will be described. Unless otherwise specified, these specific examples are not intended to limit the scope of the invention in any way, and the various materials and methods used in the examples are within the scope of the knowledge of one skilled in the art.

Example 1

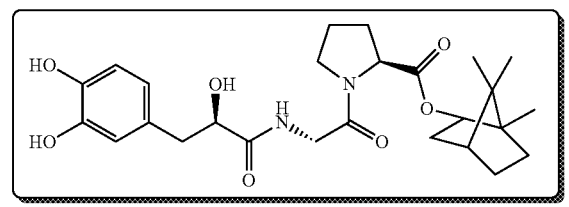
221s-1a

Step 1:

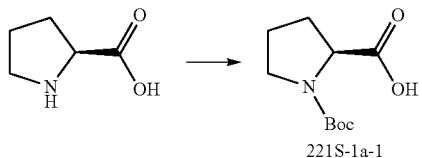
221S-1a-1

To a 1000 ml three-necked flask equipped with a thermometer, L-proline (115.1 g, 1.0 mol), 1,4-dioxane (300 mL), and 2 mol/L aqueous sodium hydroxide solution (400 mL) were added. The mixture was cooled to 0° C. and stirred for 10 minutes. After di-tert-butyl dicarbonate (283.8 g, 1.3 mol) was added dropwise (over 60 minutes), the mixture was slowly warmed, and stirred at room temperature for 6 hours or overnight. The reaction solution was adjusted to pH=4 with 4 mol/L of dilute hydrochloric acid, extracted with ethyl acetate/water system and washed three times. The organic phases were combined and dried over anhydrous sodium sulfate to obtain 189.2 g of 221S-1a-1 as white solid in 88% yield.

Step 2:

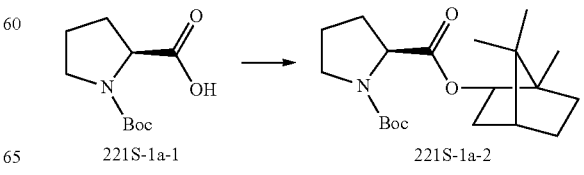
221S-1a-1              221S-1a-2

To a 500 ml three-necked flask equipped with a thermometer, 221S-1a-1(2.15 g, 10.0 mmol), tetrahydrofuran (35 mL), D-borneol (1.39 g, 9 mmol), and DMAP (0.12 g, 1 mmol) were added. The mixture was cooled to 0° C. and stirred for 5 minutes. After EDCI (2.30 g, 12 mmol) was added portionwise (over 15 min), the mixture was slowly warmed to room temperature for 24 hours. The reaction solution was extracted with ethyl acetate/water system and washed three times. The organic phases were combined and dried over anhydrous sodium sulfate and suction filtered. The resulting solid was separated by silica gel chromatography column to obtain 2.28 g of 221S-1a-2 in 60% yield.

Step 3:

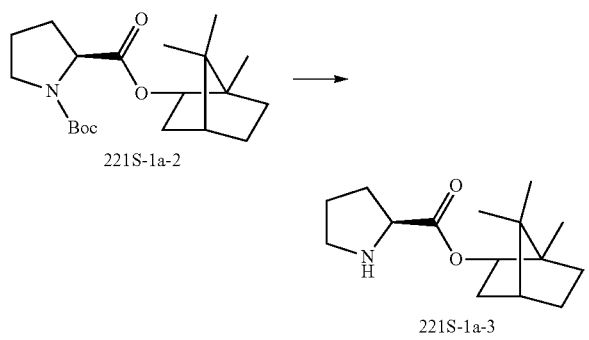

To a 500 ml single-necked flask, 221S-1a-2 (3.51 g, 10 mmol), trifluoroacetic acid (8 mL), and dichloromethane (16 mL) were added. The mixture was stirred at room temperature under a nitrogen atmosphere for 5 hours, concentrated under reduced pressure, and after addition of ethyl acetate (50 mL), water (50 mL), and saturated aqueous sodium bicarbonate solution (50 mL), was extracted three times. The organic phases were combined, dried over anhydrous sodium sulfate, suction filtered and concentrated under reduced pressure, to obtain 2.2 g of 221S-1a-3 as a pale yellow oil or semi-solid in 88% yield. The product was used directly in the next step without further purification.

Step 4:

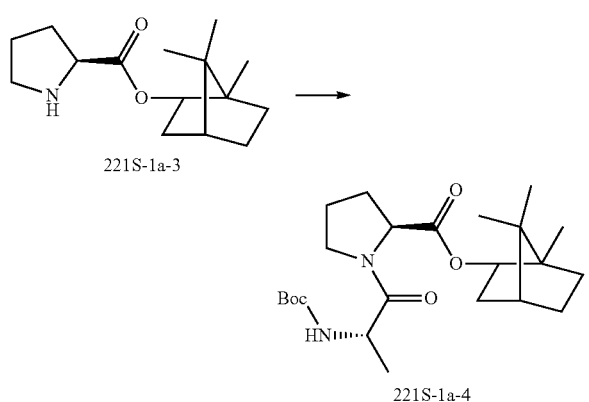

To a 250 ml single-necked flask, 221S-1a-3 (2.51 g, 10 mmol), N-Boc-Ala (2.08 g, 11 mmol), dichloromethane (50 mL), HOBT (1.49 g, 11 mmol), and EDCI (2.30 g, 12 mmol) were added. The mixture was stirred overnight at room temperature under a nitrogen atmosphere, concentrated under reduced pressure, and after addition of ethyl acetate (50 mL), water (50 mL), and saturated aqueous sodium bicarbonate solution (50 mL), was extracted three times. The organic phases were combined, dried over anhydrous sodium sulfate, suction filtered and concentrated under reduced pressure. The resulting crude product was isolated by silica gel chromatography column to obtain 3.85 g of 221S-1a-4 as a pale yellow oil in 91.2% yield.

MS m/z=[M+1]423. 2900

$^1$H NMR (600 MHZ, CDCl$_3$) δ 5.39 (d, J=8.0 Hz, 1H), 4.96 (d, J=9.7 Hz, 1H), 4.56 (dd, J=8.4, 3.9 Hz, 1H), 4.52-4.44 (m, 1H), 3.65-3.58 (m, 1H), 2.38-2.30 (m, 1H), 2.27-2.20 (m, 1H), 2.09-1.97 (m, 3H), 1.90-1.84 (m, 1H), 1.77-1.72 (m, 1H), 1.70-1.67 (m, 1H), 1.43 (s, 9H), 1.36 (d, J=6.9 Hz, 3H), 1.33-1.21 (m, 3H), 1.03 (dd, J=13.8, 3.3 Hz, 1H), 0.89 (s, 3H), 0.86 (s, 3H), 0.80 (s, 3H).

Step 5:

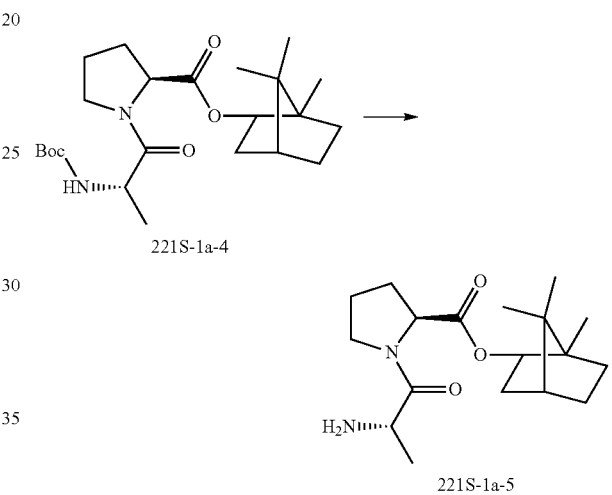

4.22 g of 221S-1a-4 was added according the procure as described in step 3, Example 1, to obtain 2.93 g of 221S-1a-5 as a light yellow or off-white solid in 91% yield. The product was used directly in the next step without further purification.

MS m/z=[M+1]323. 2386

$^1$H NMR (600 MHz, cdcl$_3$) δ 4.94 (d, J=9.7 Hz), 4.54 (dd, J=8.6, 4.4 Hz, 1H), 4.34 (d, J=6.7 Hz, 1H), 3.69-3.63 (m, 1H), 3.59-3.54 (m, 1H), 2.36-2.27 (m, 2H), 2.13-2.00 (m, 4H), 1.83-1.74 (m, 2H), 1.72-1.68 (m, 1H), 1.56 (d, J=7.0 Hz, 3H), 1.51 (d, J=6.9 Hz, 1H), 1.34-1.27 (m, 1H), 1.26-1.20 (m, 1H), 0.97 (dd, J=13.8, 3.2 Hz, 1H), 0.89 (s, 3H), 0.87 (s, 3H), 0.78 (s, 3H).

Step 6:

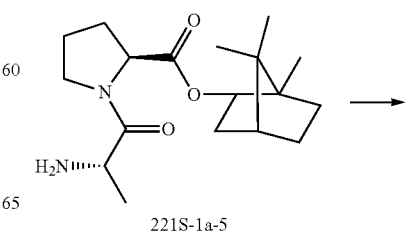

49.08 (s), 48.10 (s), 17.32 (s), 46.48 (s), 44.95 (s), 39.81 (s), 36.64 (s), 29.30 (s), 28.14 (s), 27.29 (s), 24.94 (s), 19.82 (s), 18.94 (s), 17.71 (s), 13.70 (s), 0.15 (s).

Step 7:

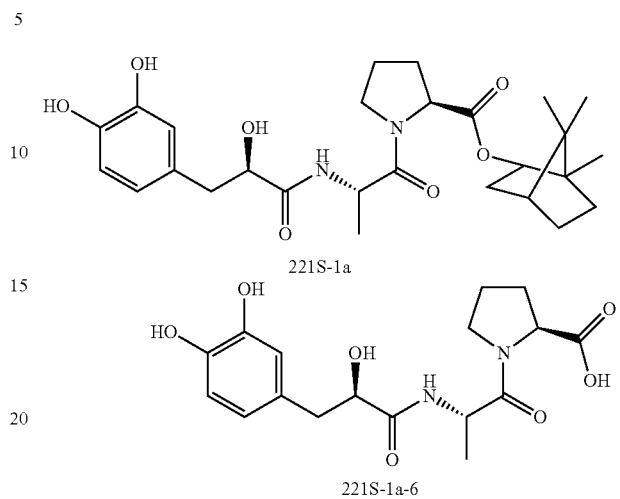

221S-1a 221S-1a-6

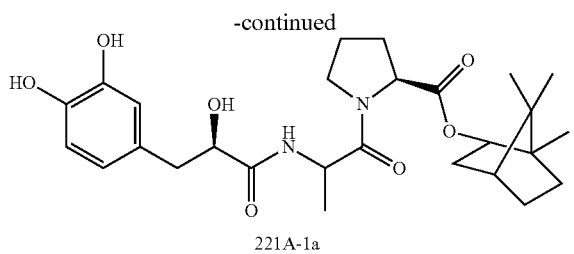

221A-1a

To a 100 ml single-necked flask, 221S-1a-5 (0.322 g, 1.0 mmol), D-Danshensu (0.22 g, 1.1 mmol), N,N-dimethylformamide (5 mL)/hexamethylphosphoramide (5 mL), HOBT (0.15 g, 1.1 mmol) and EDCI (0.18 g, 1.3 mmol) were added. The mixture was stirred for 36 hours at room temperature under nitrogen atmosphere, and after addition of ethyl acetate (50 mL), water (50 mL), and saturated aqueous sodium bicarbonate solution (50 mL), was extracted three times. The organic phases were combined, dried over anhydrous sodium sulfate, suction filtered and concentrated under reduced pressure. The resulting crude product was isolated by silica gel column chromatography to obtain 0.28 g of 221S-1a as a off-white or light white foam solid in 56% yield.

MS m/z=[M+1]: 503.0

$^1$H NMR (600 MHz, CDCl$_3$) δ 8.16 (s, 1H), 7.42 (d, J=8.1 Hz, 1H), 6.81 (d, J=8.0 Hz, 1H), 6.71 (s, 1H), 6.65 (d, J=9.8 Hz, 1H), 5.85 (s, 1H), 4.93 (d, J=9.0 Hz, 1H), 4.81-4.73 (m, 1H), 4.31-4.26 (m, 1H), 4.23 (dd, J=8.6, 4.3 Hz, 1H), 3.81 (dd, J=17.0, 7.3 Hz, 1H), 3.68-3.59 (m, 1H), 3.34 (d, J=4.6 Hz, 1H), 3.10 (dd, J=14.1, 3.9 Hz, 1H), 2.96 (dd, J=14.1, 8.1 Hz, 1H), 2.37-2.31 (m, 1H), 2.25-2.17 (m, 1H), 2.12-2.01 (m, 2H), 1.94-1.02 (m, 1H), 1.90-1.84 (m, 1H), 1.79-1.73 (m, 1H), 1.68 (t, J=4.4 Hz, 1H), 1.40 (d, J=7.0 Hz, 3H), 1.35-1.20 (m, 3H), 1.02 (dd, J=13.8, 3.4 Hz, 1H), 0.88 (s, 3H), 0.86 (s, 3H), 0.80 (s, 3H).

$^{12}$C NMR (600 MHz, CDCl$_3$) δ173.49 (s), 171.96 (s), 171.74 (s), 144.03 (s), 143.97 (s), 128.27 (s), 121.54 (s), 116.89 (s), 115.15 (s), 81.17 (s), 72.79 (s), 59.51 (s),

To a 100 ml single-necked flask, 221S-1a (0.251 g, 0.5 mmol), Lithium hydroxide (0.05 g, 2.0 mmol), water:methanol:tetrahydrofuran in 3:1:1 (10 mL) were added. The mixture was stirred for 16 hours at room temperature under nitrogen atmosphere, and after addition of ethyl acetate (30 mL) and water (30 mL), was extracted three times. The organic phases were combined, dried over anhydrous sodium sulfate, suction filtered and concentrated under reduced pressure. The resulting crude product was isolated by silica gel column chromatography to obtain 0.14 g of 221S-1a-6 as an off-white or light white foam solid in 76% yield. MS m/z=[M+1], 366.9

The following compound examples 2-28 of formula (I) were prepared according to the procedure described in example 1 above, using appropriate starting materials and reagents.

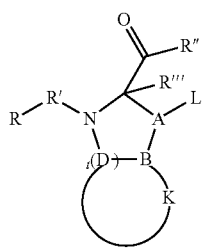

(I)

| Example | No. | Structure formula | molecular formula | MS ESI +ve m/z: [M + 1]$^+$, calculated | measured |
|---|---|---|---|---|---|
| 2 | 221S-1b | 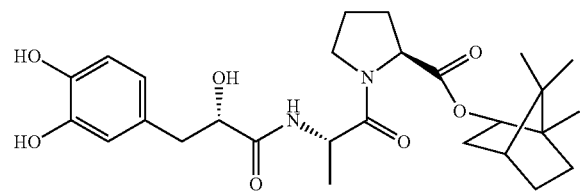 | C$_{27}$H$_{38}$N$_2$O$_7$ | 503.3 | 503.0 |

-continued
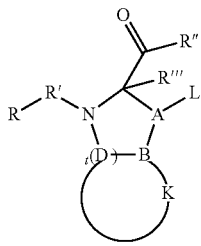
(I)
| Example | No. | Structure formula | molecular formula | MS ESI +ve m/z: [M + 1]⁺, calculated | measured |
|---|---|---|---|---|---|
| 3 | 221S-2a | | $C_{29}H_{42}N_2O_7$ | 531.3 | 531.0 |
| 4 | 221S-3a | | $C_{30}H_{44}N_2O_7$ | 545.3 | 545.0 |
| 5 | 221S-4a | | $C_{30}H_{44}N_2O_7$ | 545.3 | 545.0 |
| 6 | 221S-5a | | $C_{30}H_{44}N_2O_7$ | 545.3 | 545.0 |
| 7 | 221S-6a | | $C_{29}H_{40}N_2O_7$ | 529.3 | 529.0 |

-continued
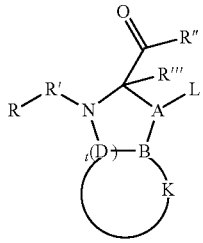
(I)
| Example | No. | Structure formula | molecular formula | MS ESI +ve m/z: [M + 1]+, calculated | measured |
|---|---|---|---|---|---|
| 8 | 221S-7a | | $C_{29}H_{42}N_2O_7S$ | 563.3 | 563.0 |
| 9 | 221S-8a | | $C_{33}H_{42}N_2O_7$ | 579.3 | 579.0 |
| 10 | 221S-9a | | $C_{34}H_{44}N_2O_7$ | 593.3 | 593.0 |
| 11 | 221S-11a | | $C_{27}H_{38}N_2O_7$ | 503.3 | 503.0 |
| 12 | 221S-12a | | $C_{28}H_{40}N_2O_7$ | 517.3 | 517.0 |

-continued
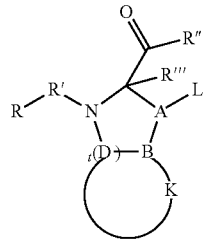
(I)
| Example | No. | Structure formula | molecular formula | MS ESI +ve m/z: [M + 1]+, calculated | measured |
|---|---|---|---|---|---|
| 13 | 221S-14a | | $C_{28}H_{40}N_2O_8$ | 533.3 | 533.0 |
| 14 | 221S-15a | | $C_{26}H_{36}N_2O_7$ | 489.3 | 489.0 |
| 15 | 221S-22a | | $C_{27}H_{38}N_2O_6$ | 487.3 | 487.0 |
| 16 | 221S-27a | | $C_{28}H_{38}N_2O_6$ | 499.3 | 499.0 |
| 17 | 221S-28a | | $C_{27}H_{36}N_2O_6$ | 485.3 | 485.0 |
| 18 | 221S-29a | | $C_{26}H_{36}N_2O_6$ | 473.3 | 473.0 |

-continued
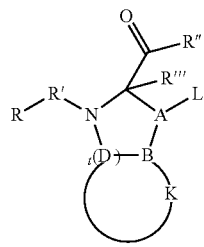
(I)
| Example | No. | Structure formula | molecular formula | MS ESI +ve m/z: [M + 1]+, calculated | measured |
|---|---|---|---|---|---|
| 19 | 221S-30a | | $C_{25}H_{34}N_2O_6$ | 459.2 | 458.9 |
| 20 | 221S-31a | | $C_{25}H_{34}N_2O_7$ | 475.2 | 474.9 |
| 21 | 221S-106a | | $C_{36}H_{46}N_2O_7$ | 619.3 | 619.0 |
| 22 | 221S-108a | | $C_{32}H_{46}N_2O_7S$ | 603.3 | 603.0 |

-continued
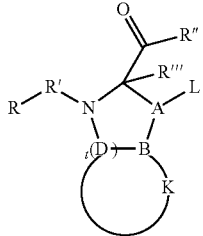
(I)
| Example | No. | Structure formula | molecular formula | MS ESI +ve m/z: [M + 1]+, calculated | measured |
|---|---|---|---|---|---|
| 23 | 221S-110a | | $C_{33}H_{48}N_2O_7$ | 585.3 | 585.0 |
| 24 | 221S-112a | | $C_{32}H_{44}N_2O_7$ | 569.3 | 569.0 |
| 25 | 221S-114a | | $C_{36}H_{52}N_2O_7$ | 625.4 | 625.0 |
| 26 | 221S-119a | | $C_{25}H_{32}N_4O_7$ | 501.2 | 500.9 |

-continued

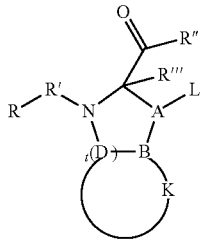

(I)

| Example | No. | Structure formula | molecular formula | MS ESI +ve m/z: [M + 1]+, calculated | measured |
|---|---|---|---|---|---|
| 27 | 221S-130a | | $C_{29}H_{36}N_2O_{10}$ | 573.2 | 572.9 |
| 28 | 221S-144a | | $C_{27}H_{40}N_2O_7$ | 505.3 | 504.0 |

The coupling agent used in the synthesis of 221S-2a and 221S-144a was T3P®; the coupling agent used in the synthesis of 7a was HATU and the base used was DIPEA; the coupling agent used in the synthesis of 221S-119a was PyBOP; and the agent used in the synthesis of 221S-11a and 221S-12a was DCC.

The synthesis of the key intermediate L-Danshensu can be found in CN 103288630, the synthesis of ligustrazine alcohol can be found in *Journal of Natural Products*, 2012, 75 (9), 1589-1594, and the synthesis of cyclohexaneproline can be found in *Org. Biomol. Chem.* 2012, 10, 2840-2846. The synthesis route of *asarum* alcohol is as follows:

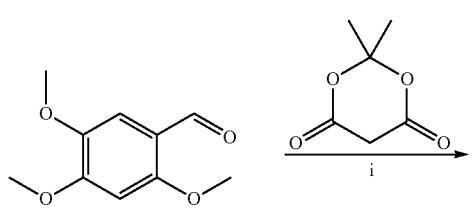

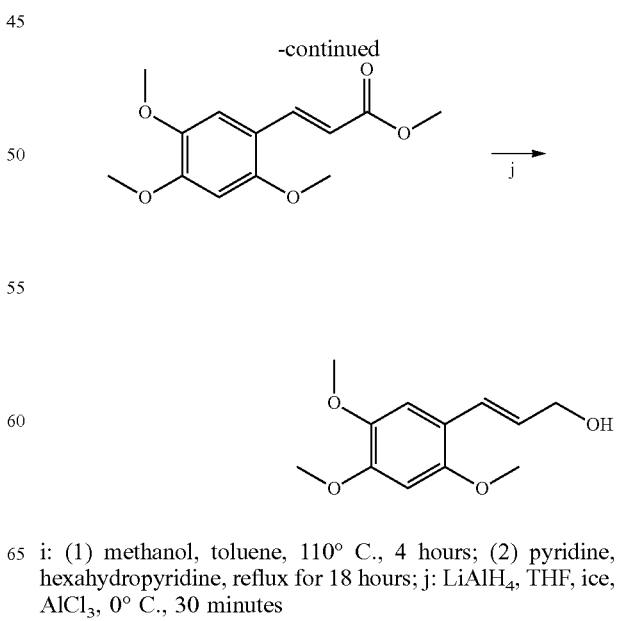

i: (1) methanol, toluene, 110° C., 4 hours; (2) pyridine, hexahydropyridine, reflux for 18 hours; j: LiAlH₄, THF, ice, AlCl₃, 0° C., 30 minutes

Example 29

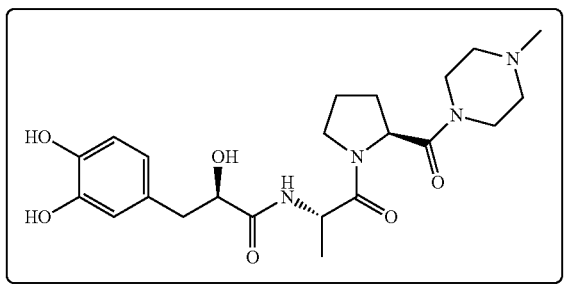

221S-151a

Step 1:

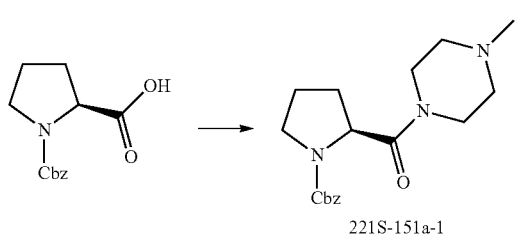

221S-151a-1

To a 500 ml three-necked flask equipped with a thermometer, N-Cbz proline (2.49 g, 10 mmol), DCM (50 mL), 1-methylpiperazine (1.10 g, 11 mmol), and DMAP (0.12 g, 1.0 mmol) were added. The mixture was cooled to 0° C. and stirred for 5 minutes. After EDCI (2.30 g, 12 mol) was added portionwise (over 15 minutes), the mixture was slowly warmed, and at room temperature for 24 hours. The reaction solution was extracted with ethyl acetate/water system and washed three times. The organic phases were combined, dried over anhydrous sodium sulfate and suction filtered. The resulting solid was separated by silica gel chromatography column to obtain 2.91 g of 221S-151a-1 in 88% yield.

Step 2:

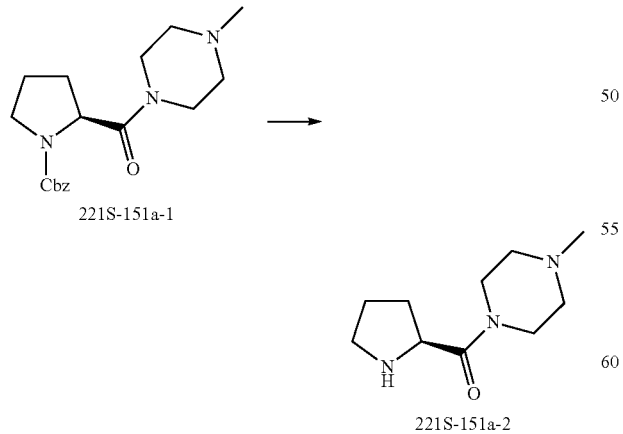

221S-151a-1

221S-151a-2

To a 500 ml three-necked flask, 221S-151a-1 (1.66 g, 5 mmol), palladium on carbon (0.16 g), and methanol (25 mL) were added, and hydrogen gas was introduced. The mixture was stirred at room temperature under normal pressure for 24 hours. The palladium on carbon was removed by filtration, and the filtrate was subjected to rotary evaporation under reduced pressure. The resulting oil was separated by silica gel chromatography column to obtain 0.89 g of 221S-151a-2 in 90% yield.

Step 3:

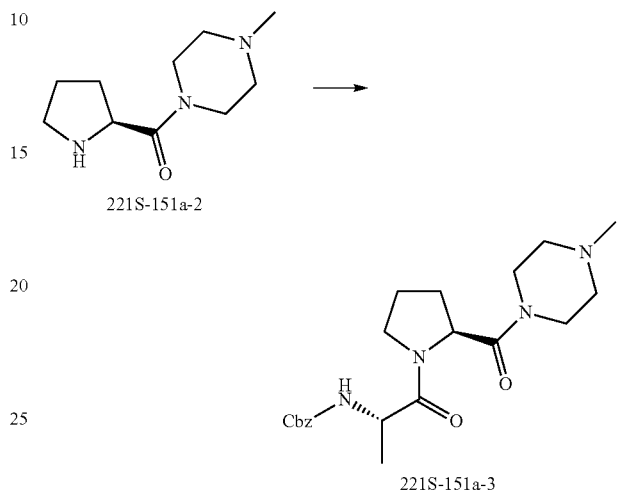

221S-151a-2

221S-151a-3

To a 500 ml three-necked flask equipped with a thermometer, 221S-151a-2 (1.97 g, 10 mmol), DCM (50 mL), N-Cbz alanine (2.45, 11 mmol) and DMAP (0.12 g, 1.0 mmol) were added, respectively. The mixture was cooled to 0° C. and stirred for 5 minutes. After EDCI (2.30 g, 12 mol) was added portionwise (over 15 minutes), the mixture was slowly warmed, and at room temperature for 24 hours. The reaction solution was extracted with ethyl acetate/water system and washed three times. The organic phases were combined, dried over anhydrous sodium sulfate and suction filtered. The resulting solid was separated by silica gel chromatography column to obtain 3.26 g of 221S-151a-3 in 81% yield.

Step 4:

221S-151a-3

221S-151a-4

According to the same procedure as step 2 of Example 29, 4.02 g of 221S-151a-3 was added to obtain 2.01 g of 221S-151a-4 in 75% yield.

Step 5:

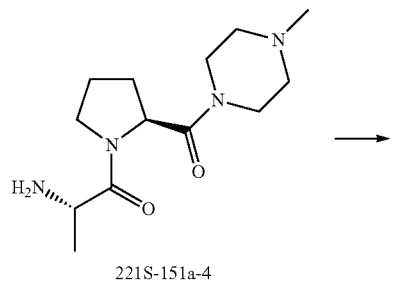

221S-151a-4

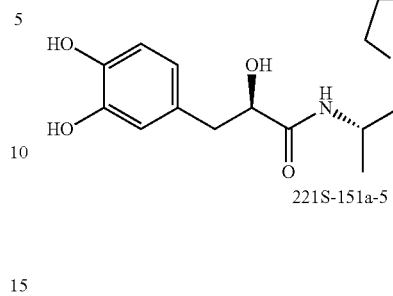

221S-151a-5

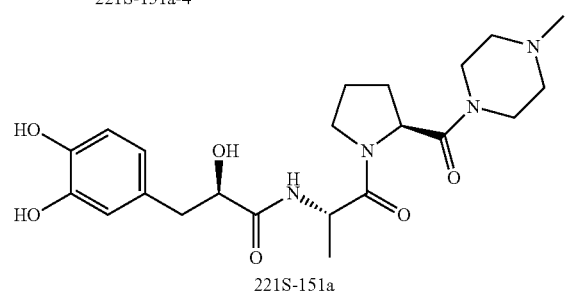

221S-151a

According to the same procedure as step 6 of Example 1, 0.27 g of 221S-151a-4 was added to obtain 0.27 g of 221S-151a in 61% yield.

Step 6:

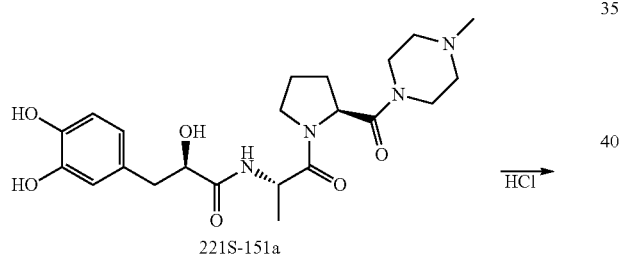 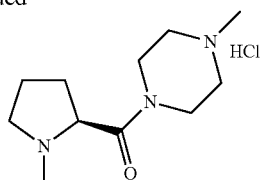

221S-151a

To a 500 ml three-necked flask, 221S-151a (0.45 g, 1 mmol), and methanol (25 mL) were added. The mixture was cooled to 0° C. and stirred for 5 minutes, and after slow introduction of hydrochloric acid gas, stirred at 2-4° C. for 4 hours, then suction filtered to obtain 0.40 g of 221S-151a-5 in 83% yield.

Other compounds containing amines can be prepared in the same manner into hydrochloride salt. In addition, other acid salts can be prepared in a similar manner, wherein corresponding acid was slowly added into a solvent containing an amine compound, and the mixture was stirred at low temperature (2-4° C.) or room temperature for 2-10 hours to obtain the corresponding acid salt.

Examples 30-35

The following compounds were prepared according to the procedure described in Example 19 mentioned above, using appropriate starting materials and reagents.

TABLE 2

| Example | No. | Structure formula | molecular formula | MS ESI +ve m/z: [M + 1]+, calculated | measured |
|---|---|---|---|---|---|
| 30 | 221S-149a | | $C_{20}H_{30}N_4O_6$ | 423.2 | 422.9 |
| 31 | 221S-150a | | $C_{21}H_{28}FN_3O_6S$ | 470.2 | 469.9 |

TABLE 2-continued

| Example | No. | Structure formula | molecular formula | MS ESI +ve m/z: [M + 1]+, calculated | measured |
|---|---|---|---|---|---|
| 32 | 221S-152a | | $C_{21}H_{32}N_4O_6$ | 437.2 | 436.9 |
| 33 | 221S-153a | | $C_{21}H_{28}N_4O_6$ | 433.2 | 432.9 |
| 34 | 221S-158a | | $C_{24}H_{36}N_4O_7$ | 493.3 | 493.0 |
| 35 | 221S-161a | | $C_{27}H_{40}N_4O_7$ | 533.3 | 533.0 |

In the synthesis of 221S-153a, proline and alanine were protected with Boc, and the Boc-deprotection reaction was carried out according to Step 2 of Example 1.

Example 36

221S-177a

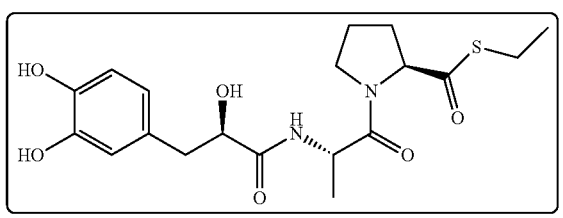

Step 1:

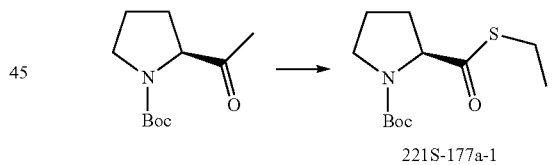

221S-177a-1

N-Boc proline (21.5 g, 0.1 mol), DCC (20.6 g, 1.0 mol), DMAP (1.22 g, 0.01 mmol) were added sequentially to 150 mL of DMF The reaction mixture was stirred at room temperature for 10 minutes and then cooled to 0° C. After ethanethiol (6.82 g, 0.11 mol) was added dropwise, the reaction was left overnight, 200 mL of water was added to the reaction system to quench the reaction. The reaction mixture was filtered and the filter cake was washed with ethyl acetate to remove DCU. The organic phases were combined, washed successively with saturated aqueous sodium carbonate solution (20 mL×3), water and saturated aqueous sodium chloride solution, dried over anhydrous magnesium sulfate, filtered and concentrated. After purification by a low pressure column chromatography, 18.4 g of product 221S-177a-1 was obtained in 71% yield.

Step 2:

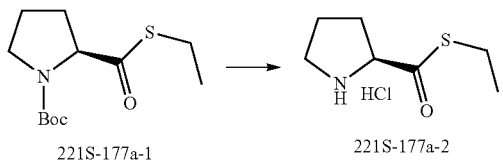

221S-177a-1 (2.59 g, 10 mmol) was dissolved in EtOAc (25 mL) and stirred well. HCl gas was bubbled at room temperature for 30 minutes, and then the remaining HCl gas was blown off by nitrogen gas. The mixture was subjected to rotary evaporation under reduced pressure, followed by vacuum drying, to obtain 1.66 g of 221S-177a-2 as white solid in 85% yield.

Step 3:

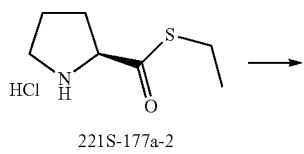

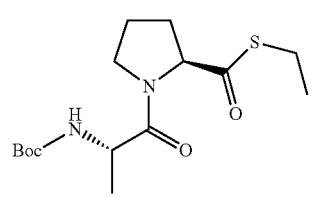

221S-177a-3

To a 250 mL single-necked flask, 221S-117a-2 (1.98 g, 10 mmol), N-Boc-alanine (2.08 g, 11 mmol). DCM (50 mL), HOBT (1.49 g, 11 mmol), and EDCI (2.30 g, 12 mmol) were added. The mixture was stirred overnight at room temperature under nitrogen gas protection, concentrated under reduced pressure, and after addition of ethyl acetate (50 mL), water (50 mL), and saturated aqueous sodium bicarbonate solution (50 mL), was extracted three times. The organic phases were combined, dried over anhydrous sodium sulfate, suction filtered and concentrated under reduced pressure. The resulting crude product was isolated by silica gel column chromatography to obtain 2.51 g of 221S-177a-3 as pale yellow oil in 76% yield.

Step 4:

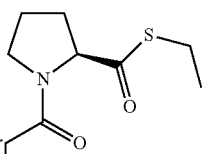

221S-177a-3

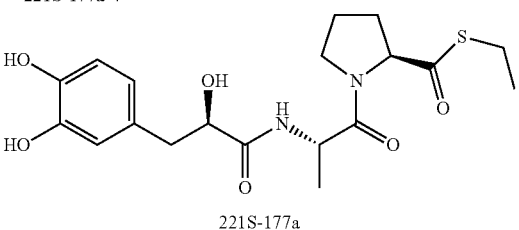

221S-177a-4

According to the same procedure as step 5 of Example 1, 3.3 g of 221S-177a-3 was added to obtain 1.66 g of 221S-177a-4 as a off-white solid in 74% yield. MS ESI +ve m/z: 231.9. The product was used directly in the next step without further purification.

Step 5:

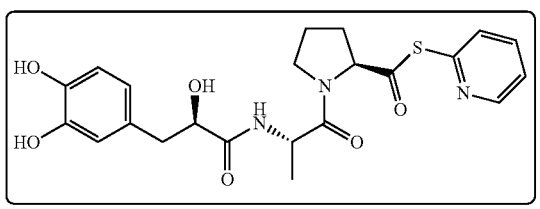

According to the same procedure as Step 6 of Example 1, 0.23 g of 221S-177a-4 was added to obtain 0.22 g of 221S-177a in 51% yield. MS ESI +ve m/z: 411.2.

Example 37

221S-181a

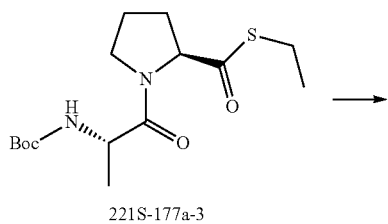

Step 1:

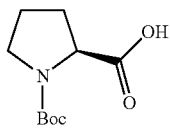

In dry THF (40 mL). N-Boc (2.15 g, 10 mmol) was dissolved and then 2,2'-dithiopyridine (2.20 g, 10 mmol) and triphenylphosphine (3.14 g, 12 mmol) were added. The mixture was stirred at room temperature for 3 hours and extracted with ethyl acetate/water system. The organic phases were combined, washed with water, saturated aqueous sodium chloride solution, dried over anhydrous magnesium sulfate, filtered and concentrated. After purification by a low pressure column chromatography, 2.46 g of product 221S-181a-1 was added in 80% yield.

Step 2:

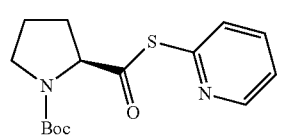

221S-181a-1

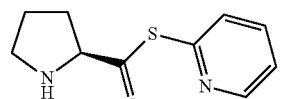

221S-181a-2

According to the same procedure as Step 3 of Example 1, 3.08 g of 221S-181a-1 was added to obtain 1.62 g of 221S-181a-2 in 78% yield. MS ESI +ve m/z: 209.0.

Step 3:

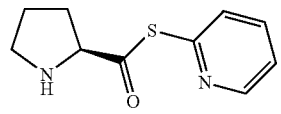

221S-181a-2

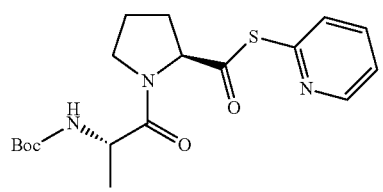

221S-181a-3

According to the same procedure as Step 4 of Example 1, 2.08 g of 221S-181a-2 was added to obtain 3.31 g of 221S-181a-3 in 87% yield. MS ESI +ve m/z: 379.9.

Step 4:

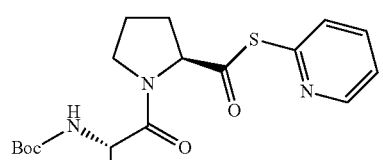

221S-181a-3

-continued

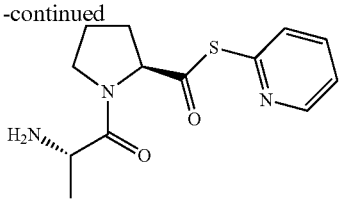

221S-181a-4

According to the same procedure as Step 3 of Example 1, 3.80 g of 221S-181a-3 was added to obtain 2.0 g of 221S-181a-4 in 73% yield. MS ESI +ve m/z: 279.9.

Step 5:

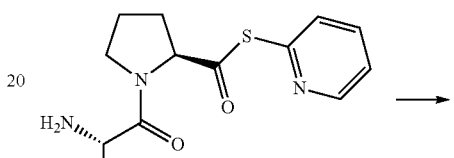

221S-181a-4

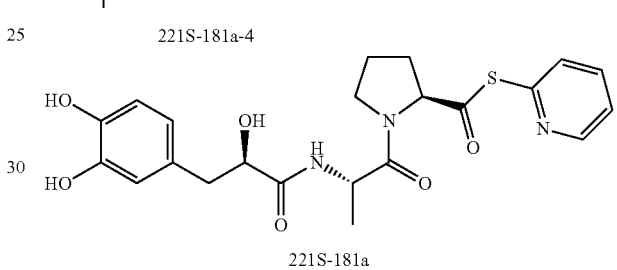

221S-181a

According to the same procedure as Step 6 of Example 1, 0.28 g of 221S-181a-4 was added to obtain 0.22 g of 221S-181 in 48% yield. MS ESI +ve m/z: 460.0

Example 37

Step 1:

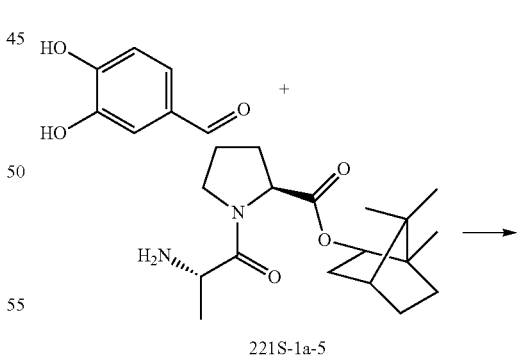

221S-1a-5

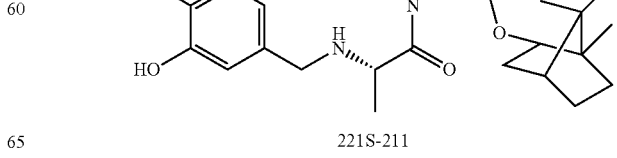

221S-211

To a 250 mL single-necked flask, 221S-1a-5 (0.32 g, 1.0 mmol), protocatechualdehyde (0.166 g, 1.2 mmol), dichloroethane (25 mL), sodium cyanoborohydride (0.10 g, 1.5 mmol) and 2 drops of acetic acid were added. The mixture was at room temperature under nitrogen gas protection for 6 hours, concentrated under reduced pressure, and after addition of ethyl acetate (50 mL), water (50 mL), and saturated aqueous sodium bicarbonate solution (50 mL), extracted three times. The organic phases were combined, dried over anhydrous sodium sulfate, suction filtered and concentrated under reduced pressure. The resulting crude product was isolated by silica gel chromatography column to obtain 0.15 g of 221S-221 as pale yellow oil in 34% yield.

Step 2:

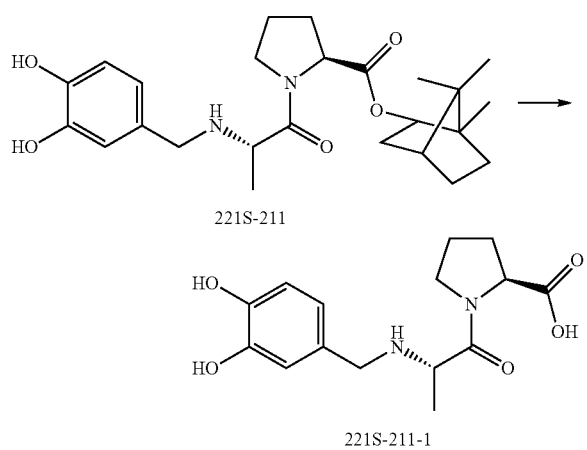

221S-211

221S-211-1

According to the same procedure as Step 7 of Example 1, 0.44 g of 221S-221 was added to obtain 0.16 g of 221S-221-1 in 52% yield. MS ESI +ve m/z: 309.2.

The specific examples described in the present invention are merely illustrative description of the spirit of the present invention. It will be apparent to those skilled in the art to which this invention pertains that various modifications, additions and alternatives may be made to the described specific embodiments without departing from the spirit of the invention or as defined in the appended claims.

LC-MS Test Method of the Invention

LC-QTOF MS & MS/MS conditions: HPLC equipment: Agilent 1200 Infinity LC; column: Agilent HC-C18 4.6×250 mm, 5 µm; flow rate: 0.6 mL/min; column temperature: 30° C.; Mobile phase: A-$H_2O$, 0.1% acetic acid/B-methanol, A:B=20:80; MS equipment: Agilent 6520 QTOF; ion source: Dual ESI; ion mode: positive; ion spray voltage: 3500 V; dry gas temperature: 350° C.; dry gas flow rate: 10.0 L/min. ($N_2$); sprayer pressure: 45 psi (N2); breaker voltage: 130 V; collision energy: 10, 25 and 40 eV, respectively.

The present invention relates to novel angiotensin converting enzyme inhibitors and their biological activity is further described by the following in vivo and in vitro assays.

Determination of Angiotensin-Converting Enzyme (ACE) Activity

In Vitro ACE Activity Test

High Performance Liquid Chromatography assay: Reference is made to the method described in Cushman et al. (*Biochemical Pharmacology*, 1971, 20 (7): 1637-1648; *Journal of Dairy Science*, 1995, 78 (4): 777-783), the angiotensin-converting enzyme activity of the compounds of the present invention were assayed using the reported method. This method was based on the content of hippuric acid (Hip), a hydrolyzate of the Ang 1 mimic hippuryl-histidyl-leucine (HHL), which is suitable for continuous monitoring of ACE activity. Upon the addition of an ACE inhibitor, the progress of the reaction can be inhibited, thereby reducing the production of hippuric acid. Thus, ACE inhibitory activity is obtained by measuring the change in UV absorbance at 228 nm of hippuric acid produced before and after the addition of the inhibitor.

Material and Method:
(1) Material:
Experimental Apparatus:

TABLE 3

Experimental apparatus for in vitro activity test

| Device/instrument name | model | manufacturer |
|---|---|---|
| Microplate reader | MULTISKAN GO | Thermo, US |
| Vortex mixer | VORTEX-6 | Haimen Qilin Bei'er, China |
| Analytical balance | Mettler Toledo XS105 | Mettler-Toledo International Gmbh |
| pH meter | PHS-3C | Shanghai Leici instrument factory |
| Thermostatic water bath oscillators | THZ-82 | Guohua, China |

Experimental Reagents:

TABLE 4

Experimental reagents for in vitro activity test

| chemical name | specification | manufacturer |
|---|---|---|
| ACE | | Sigma |
| Hip | AR | Sigma |
| HHL | AR | Sigma |
| HEPES | | Sigma |

(2) Experimental Method

A mixture of 25 µl of sample solution (dissolved in 50 mM HEPES hydrochloric acid buffer, pH=8.3, containing 300 mM NaCl, 50 µmol) and 200 µl of 3% substrate HHL (dissolved in the same buffer) were kept at 37° C. for 6 min. After the addition of 50 µl of ACE (0.5 U, dissolved in 1.5 mL of the same buffer), the reaction was carried out at 37° C. for 15 minutes, then 250 µl of 1 mol/L hydrochloric acid was added to stop the reaction. The reaction mixture was mixed evenly and allowed to stand for 5 min. After 2 mL of ethyl acetate was added, the mixture was vigorously shaken for 60 s and centrifuged at 1000×g for 10 min. The supernatant was placed in boiling water bath for 15 min, and after the addition of 3 mL of deionized water, mixed and allowed to stand, 20 uL of reactants was loaded for detecting hippuric acid by reversed phase high performance liquid chromatography. The inhibitory effect of the sample on ACE was judged by the amount of hippuric acid produced, and the buffer was used in place of sample solution as a blank control, inhibition rate of the sample on ACE (%)=(peak value of the control hippuric acid−peak value of the sample hippuric acid)/peak value of the control hippuric acid× 100%.

Chromatographic Conditions:

Ultraviolet detector; wavelength: 228 nm; Column: Agilent HC-$C_{18}$ 4.6×250 mm, 5 µm; Flow rate: 1.0 mL/min; Injection volume: 20 µL; Column temperature: 30° C.; Mobile phase: acetonitrile-water (80/20). The results are shown in Table 5:

TABLE 5

| Compound No. | Formular | IC$_{50}$ (nM) |
|---|---|---|
| Captopril | | 28 ± 6 |
| 221S-15a | | 33 ± 6 |
| 221S-1a | | 23 ± 9 |
| 221S-2a | | 37 ± 5 |
| 221S-3a | | 27 ± 7 |
| 221S-4a | | 34 ± 7 |

TABLE 5-continued

| Compound No. | Formular | IC$_{50}$ (nM) |
| --- | --- | --- |
| 221S-5a | | 28 ± 9 |
| 221S-8a | | 65 ± 5 |
| 221S-7a | | 78 ± 5 |
| 221S-6a | | 43 ± 6 |
| 221S-1b | | 33 ± 6 |
| 221S-28a | | 29 ± 7 |

TABLE 5-continued

| Compound No. | Formular | IC$_{50}$ (nM) |
|---|---|---|
| 221S-27a | | 44 ± 3 |
| 221S-29a | | 38 ± 5 |
| 221S-30a | | 35 ± 6 |
| 221S-31a | | 31 ± 8 |

In Vivo ACE Activity Test

Material and Method:

Experimental Apparatus:

TABLE 6

Experimental apparatus for in vivo activity test

| Device/ instrument name | model | manufacturer |
|---|---|---|
| Microplate reader | MULTISKAN GO | Thermo, US |
| Vortex mixer | VORTEX-6 | Haimen Qilin Bei'er, China |
| Analytical balance | Mettler Toledo XS105 | Mettler-Toledo International Gmbh |
| pH meter | PHS-3C | Shanghai Leici instrument factory |
| Tissue homogenizer | DY-89-1I | NingBo Scientz Biotechnology Co. |
| Thermostatic water bath oscillators | THZ-82 | Guohua, China |

Experimental Materials:

TABLE 7 experimental materials and reagents for in vivo activity test

| chemical name | specification | manufacturer |
|---|---|---|
| 221S compounds | Purity >95% | homemade |
| Captopril | Purity >98% | National Institutes for Food and Drug Control |
| Mouse angiotensin converting enzyme Enzyme-linked immunosorbent assay kit | 96-well plate | Elabscience Biotechnology Co., Ltd |
| Kunming mice | male | Xi'an Jiaotong University Health Science Center |
| PBS | pH = 7.2 | homemade |

Experimental Principle:

Determination of ACE content through double antibody sandwich ELISA method: anti-mouse ACE antibody was coated on the enzyme plate, and in the experiment, mouse ACE in the sample or standard bound to the coated antibody, and free ingredients were washed away. Biotinylated anti-mouse ACE antibodies and horseradish peroxidase-labeled avidin were added sequentially. The anti-mouse ACE antibody was bound to the mouse ACE bound to the coated antibody, and biotin specifically bound to avidin, thus an immune complex was formed and the free components were washed away. A chromogenic substrate (TMB) was added, which showed blue under the catalysis of horseradish peroxidase, and became yellow after the addition of stop solution. OD value was measured at the wavelength of 450 nm using the microplate reader. A quadratic nonlinear relationship between ACE concentration and OD450 value was showed, and the concentration of ACE in the sample was calculated by drawing a standard curve.

Experimental Methods:

(1) Treatment of the Experimental Animals 108 male Kunming mice weighing 20±2 g were randomly divided into 18 groups, including normal control group, positive control captopril group, and compound 221S group, respectively, with 6 mice per group. Animals in each group were given an intragastric administration at 0.05 mmol/kg (10 ml/kg), once a day, for 7 continuous days. 2 h after the final intragastric administration, the mice were sacrificed by cervical dislocation, and the heart, liver, brain, lung, kidney and blood were taken. The kidney was used for the test and other tissue samples were used for other experimental tests. The kidneys were diluted 10 times with PBS, homogenized, centrifuged, and the supernatant was used for the assay or stored at −20° C.

(2) Operation of ELISA

The levels of ACE in the kidney tissues of mice were detected by ELISA. All the steps were carried out strictly according to the instructions. The main steps were as follows:

(a) addition of the sample: the blank well (the blank control well was not filled with the samples and reagents, but the other steps were kept), the standard well, and the sample-to-be-measured wells were set up, respectively. 100 µL of standard solution or the sample to be tested was added to the remaining wells carefully at different concentrations. Be ensure there was no air bubbles. The mixture was then gently mixed. The plate was covered with a lid and reaction was performed at 37° C. for 90 min.

(b) The liquid was discarded, and the plate was spin dried without washing. 100 µL of biotinylated antibody working solution (prepared within 15 minutes prior to use) was added to each well. The plate was covered with a membrane and incubated at 37° C. for 1 hour.

(c) The liquid in the well was discarded, and the plate was spin dried and washed 3 times. During the washing, the plate was soaked for 1-2 minutes with about 350 µL/well, spin-dried and the liquid in the well was removed by patting gently the plate on an absorbent paper.

(d) 100 µL of enzyme conjugate working solution (prepared within 15 minutes before use) was added to each well. The plate was covered with a membrane and incubated at 37° C. for 30 min.

(e) The liquid in the well was discarded, and the plate was spin dried and washed 5 times with the same procedure as step (c).

(f) 90 µL of substrate solution (TMB) was added into each well and the plate was covered with a membrane and incubated at 37° C. in the dark for 15 min (appropriately shortened or extended depending on the actual development, but not more than 30 minutes, and stopped when a significant gradient occurred in the standard wells).

(g) 50 µL of stop solution was added into each well to stop the reaction, where the blue immediately turned into yellow. The order of addition of the stop solution should be the same as that of the substrate solution.

(h) Optical density (OD) of each well was determined at 450 nm using a microplate reader. The power of the microplate reader should be turned on in advance to warm up the instrument and set the test procedure.

The above experimental data are expressed as $\bar{x}\pm SD$ (SPSS19.0 statistical software, t-test method was used for statistical treatment).

The experimental results were shown in FIG. 1. Formula: $y=ax^2+bx+c$; where a: −0.0052; b: 0.2556; c: −0.0233; $R^2$: 0.9968.

The in vivo activity (ELISA) results were shown in Table 8:

TABLE 8

| group | dose | Number of animals | ACE content (pg/ml) |
|---|---|---|---|
| blank control | water (dose is showed below) | 6 | 111 + 9 |
| Captopril | 0.05 mmol/kg | 6 | 91 ± 9 |
| 221S-15a | 0.05 mmol/kg | 6 | 83 ± 11 |
| 221S-1a | 0.05 mmol/kg | 6 | 64 ± 8 |
| 221S-2a | 0.05 mmol/kg | 5 | 87 ± 8 |
| 221S-3a | 0.05 mmol/kg | 6 | 79 ± 7 |
| 221S-4a | 0.05 mmol/kg | 6 | 82 ± 10 |
| 221S-5a | 0.05 mmol/kg | 6 | 89 ± 11 |
| 221S 8a | 0.05 mmol/kg | 5 | 80 ± 7 |
| 221S-7a | 0.05 mmol/kg | 6 | 71 ± 9 |
| 221S-6a | 0.05 mmol/kg | 4 | 76 ± 5 |
| 221S-1b | 0.05 mmol/kg | 6 | 78 ± 12 |
| 221S-28a | 0.05 mmol/kg | 6 | 79 ± 8 |
| 221S-27a | 0.05 mmol/kg | 5 | 82 ± 11 |
| 221S-29a | 0.05 mmol/kg | 4 | 85 ± 8 |
| 221S-30a | 0.05 mmol/kg | 5 | 75 ± 8 |
| 221S-31a | 0.05 mmol/kg | 6 | 71 ± 13 |

The results showed that the compounds of the invention could reduce the content of ACE enzyme in blood of rats, and the decrease rate was higher than that of the positive drug Captopril, wherein compound 221S-1a having the most significant reduction effect.

Determination of Blood Pressure in Spontaneously Hypertensive Rats (SHR)

Experimental Apparatus and Reagents

Experimental Apparatus

TABLE 9

Experimental apparatus for in vivo activity test

| device/instrument name | model | manufacturer |
|---|---|---|
| noninvasive multi-channel blood pressure tester | BP2000 | Visitech system |
| vortex mixer | VORTEX-6 | Haimen Qilin Bei'er, China |
| analytical balance | Mettler Toledo XS105 | Mettler-Toledo International Gmbh |

Experimental Materials:

TABLE 10 experimental materials and reagents for in vivo activity test

| chemical name | specification | manufacturer |
|---|---|---|
| 221S compounds | purity >95% | homemade |
| Captopril | purity >98% | National Institutes for Food and Drug Control |
| SHR rat | male | Beijing Vital River Laboratory Animal Technology Co., Ltd. |

Experimental Methods:

SPF grade male spontaneously hypertensive model rats (SHR) (male, 12 weeks old, body weight 200 g±20 g) were divided into three groups: blank group, control group and sample group, with 6 rats each group. Animals were housed in the Shaanxi Provincial Biomedical Animal Laboratory at the School of Life Sciences of Northwest University at a temperature of 22° C. and a humidity of 50%, with 12 hours light/dark cycle and free to eat and drink water. The SHR rats were trained to adapt to blood pressure measurements after 5 days of adaptation to the environment. Prior to administration, the basal blood pressure of the rats in each group was measured and the systolic blood pressure was between 190±5 mmHg.

Determination of Blood Pressure in the SHR Rats after One Administration:

The systolic blood pressure of the experimental rats was measured by tail pulse indirect pressure measurement.

The SHR rats were administered intragastrically, wherein the sample and reference substance (captopril) were both dissolved in distilled water containing 1% Tween 80, and the blank control group was administered intragastrically the same volume of distilled water containing 1% Tween 80. The amount for intragastric administration was 0.05 mmol/kg (10 ml/kg in volume), and the blood pressure was measured at 1 h, 2 h, 3 h, 4 h and 6 h after intragastric administration, respectively.

The particular measurement steps: the conscious rats were placed in the fixed box of the blood pressure meter. A heating plate at 30° C. was provided in the bottom of the fixed box, which was preheated for 10 min to expand the local blood vessels. After the rats were in a quiet state, an inflatable tubular tail tube was wrapped around the tail root of the SHR rat and a pressure electronic pulse detector was placed at the tail root of the rat, and the signal would appear on the computer screen. After the signal was stabilized, the blood pressure was measured and the 5 readings with a change in blood pressure less than 10 mmHg were recorded, with an interval of 10 seconds. The mean value was taken as the systolic blood pressure of the rats.

Figure 2:
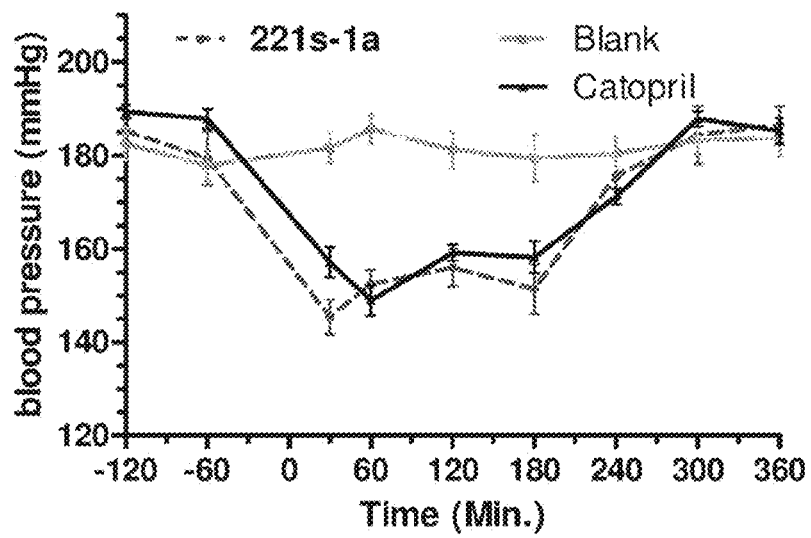
FIG. 2 shows the change of arterial systolic pressure within 6 hours after intragastric administration of 221S-1a in the SHR rats.

(a) The change of arterial systolic pressure within 6 hours after intragastric administration of 221S-1a in the SHR rats was shown in FIG. 2.

Figure 3:
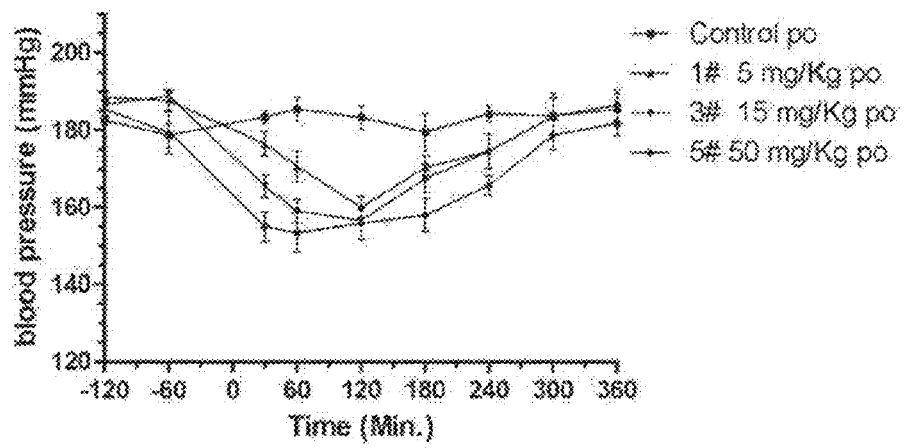
FIG. 3 shows the change of arterial systolic pressure within 6 hours after intragastric administration of 221S-1a at different doses (1#, 3#, and 5#) in the SHR rats.

(b) The change of arterial systolic pressure within 6 hours after intragastric administration of 221S-1a at different doses in the SHR rats was shown in FIG. 3.

The results shown that, compound 221S-1a showed better antihypertensive effect on SHR rats in a good dose-dependent relationship, and the antihypertensive effect was better than that of captopril.

(2) Determination of Blood Pressure in the SHR Rats after Multiple Administrations:

According to the above method and dose, rats were administered intragastrically continuously for 7 days, once a day. Blood pressure was measured 2 hours after administration. After the end of the administration, blood pressure was measured continuously for 7 days, once a day, and the change in blood pressure was recorded.

Figure 4:
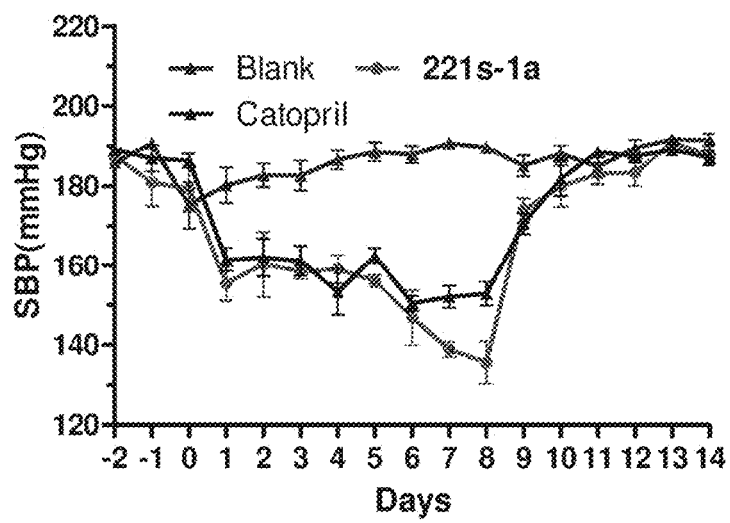
FIG. 4 shows the change of arterial systolic pressure within 14 days after intragastric administration of 221S-1a for 7 days in the SHR rats.

(a) The change of arterial systolic pressure within 14 days after intragastric administration of 221S-1a for 7 days in the SHR rats was shown in FIG. 4.

Figure 5:
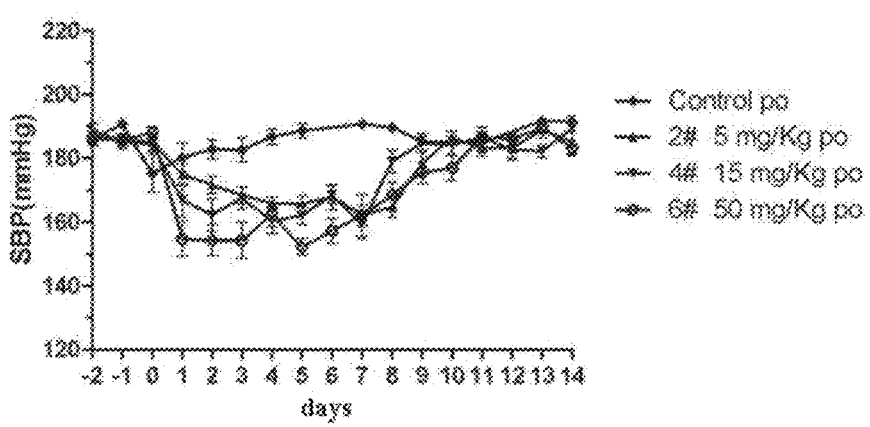
FIG. 5 shows the change of arterial systolic pressure within 14 hours after intragastric administration of 221S-1a at different doses (2#, 4#, and 6#) in the SHR rats.

(b) The change of arterial systolic pressure within 14 days after intragastric administration of 221S-1a at different doses in the SHR rats was shown in FIG. 5.

After long-term administration of compound 221S-1a for 7 days, the administration was stopped, and then the change of arterial systolic pressure within 14 days was recorded.

The results shown that, compound 221S-1a has better antihypertensive effect than captopril. The effect of different doses of 221S-1a on arterial systolic pressure in SHR rats was dose-dependent.

The above experimental data were expressed as x̄±SD (SPSS19.0 statistical software, t-test method was used for statistical treatment).

The invention claimed is:
1. A tripeptide compound with the structure of formula 221S-1a

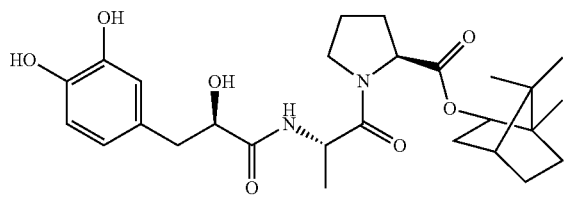

221S-1a

2. A pharmaceutically acceptable salt or a pharmaceutically acceptable ester of the compound according to claim 1, wherein the pharmaceutically acceptable salt is selected from pharmaceutically acceptable acid salt and pharmaceutically acceptable basic salt, wherein the pharmaceutically acceptable acid salt is selected from a salt formed with one of the following acids: sulfuric acid, hydrogen sulfate, hydrochloric acid, hydrobromic acid, phosphoric acid, nitric acid, carbonic acid, boric acid, methanesulfonic acid, benzenesulfonic acid, p-toluenesulfonic acid, formic acid, acetic acid, propionic acid, butyric acid, pyruvic acid, maleic acid, malic acid, tartaric acid, citric acid, ascorbic acid, benzoic acid, camphoric acid, fumaric acid, oxalic acid, succinic acid, camphorsulfonic acid, maleic acid, salicylic acid and α-lactic acid; the pharmaceutically acceptable basic salt is selected from a salt formed with one of the following bases: alkali metals selected from lithium, sodium and potassium; alkaline earth metals selected from magnesium, and calcium; lithium hydroxide, sodium hydroxide, potassium hydroxide, lithium hydride, sodium hydride, butyllithium, ammonium, triethylamine, diisopropylethylamine, ornithine, arginine, lysine and histidine; and the pharmaceutically acceptable ester is selected from an ester formed through a hydroxyl group and a phenolic hydroxyl group in the compound with an acid.

3. A solvated mixture of the compound according to claim 1, wherein the solvate is one selected from water, methanol, ethanol, isopropanol, butanol, ethyl acetate and DMSO, and a combination thereof.

4. A pharmaceutical composition comprising the compound according to claim 1, or a pharmaceutically acceptable salt thereof, and a pharmaceutically acceptable carrier, excipient or diluent.

5. A method of treating or delaying hypertension and its complications in a subject in need thereof, comprising administering the subject the compound according to claim 1, wherein the complications include one or more of coronary heart disease, chronic congestive heart failure, myocardial infarction, congestive heart disease, myocardial ischemia, myocarditis, myocardial fibrosis, myocardial hypertrophy, atherosclerosis, arrhythmia, stroke, thrombosis, diabetic nephropathy, hyperlipidemia, obesity, and hyperglycemia.

6. A method of treating or delaying hypertension and its complications in a subject in need thereof, comprising administering the subject the pharmaceutical composition according to claim 4, wherein the complications comprise one or more of coronary heart disease, chronic congestive heart failure, myocardial infarction, congestive heart disease, myocardial ischemia, myocarditis, myocardial fibrosis, myocardial hypertrophy, atherosclerosis, arrhythmia, stroke, thrombosis, diabetic nephropathy, hyperlipidemia, obesity, and hyperglycemia.

* * * * *